(12) United States Patent
Miyazaki et al.

(10) Patent No.: US 9,365,815 B2
(45) Date of Patent: Jun. 14, 2016

(54) PARTICLE SEPARATION DEVICE AND METHOD OF SEPARATING PARTICLES

(71) Applicant: National Institute of Advanced Industrial Science and Technology, Tokyo (JP)

(72) Inventors: Masaya Miyazaki, Tosu (JP); Daisuke Sugiyama, Tosu (JP); Kenichi Yamashita, Tosu (JP); Yuuki Teshima, Tosu (JP); Hiroyuki Nakamura, Tosu (JP); Hideaki Maeda, Tosu (JP)

(73) Assignee: NATIONAL INSTITUTE OF ADVANCED INDUSTRIAL SCIENCE AND TECHNOLOGY, Chiyoda-Ku, Tokyo (JP)

( * ) Notice: Subject to any disclaimer, the term of this patent is extended or adjusted under 35 U.S.C. 154(b) by 64 days.

(21) Appl. No.: 13/969,704

(22) Filed: Aug. 19, 2013

(65) Prior Publication Data

US 2014/0069849 A1 Mar. 13, 2014

(30) Foreign Application Priority Data

Sep. 10, 2012 (JP) ................................. 2012-198961

(51) Int. Cl.
*B03B 5/28* (2006.01)
*C12M 1/00* (2006.01)
(Continued)

(52) U.S. Cl.
CPC .................. *C12M 47/04* (2013.01); *B03B 5/28* (2013.01); *B01L 3/502761* (2013.01); *B01L 2300/0864* (2013.01); *B03B 2005/405* (2013.01)

(58) Field of Classification Search
CPC ............. B03B 2005/405; C12M 47/04; B01L 3/502761; B01L 2300/0864
See application file for complete search history.

(56) References Cited

U.S. PATENT DOCUMENTS

| 5,474,687 A | 12/1995 | Van Vlasselaer ............. 210/782 |
| 5,646,004 A | 7/1997 | Van Vlasselaer ............ 435/7.25 |

(Continued)

FOREIGN PATENT DOCUMENTS

| JP | 51-080378 | 7/1976 | |
| JP | 10-508190 | 8/1998 | ............... C12M 3/00 |

(Continued)

OTHER PUBLICATIONS

Morijiri, T., et al., (2011), "Sedimentation pinched-flow fractionation for size- and density-based particle sorting in microchannels", *Microfluid Nanofluid*, 11: 105-110.

(Continued)

*Primary Examiner* — Jeremy R Severson
(74) *Attorney, Agent, or Firm* — Harness, Dickey & Pierce, P.L.C.

(57) ABSTRACT

Provided are a particle separation device and a method of separating particles, each of which can easily separate particles for a short time without a great stress to the particles and easily collect the particles thus separated. The particle separation device includes at least: a separation flow path (i) to which a separation fluid and a particle group including two types of particles being different in density are supplied, and (ii) through which the separation fluid flows in a certain direction; a divergence section connected to at least an end of the separation flow path in the certain direction in which the separation fluid flows, a first flow path formed from the divergence section in a rising direction; and a second flow path formed from the divergence section in a falling direction, the separation flow path being formed in a horizontal direction.

11 Claims, 9 Drawing Sheets

(51) Int. Cl.
*B01L 3/00* (2006.01)
*B03B 5/40* (2006.01)

(56) References Cited

U.S. PATENT DOCUMENTS

| | | | |
|---|---|---|---|
| 5,648,223 A | 7/1997 | Van Vlasselaer | 435/7.23 |
| 5,663,051 A | 9/1997 | Vlasselaer | 435/7.23 |
| 5,789,148 A | 8/1998 | Van Vlasselaer et al. | 435/2 |
| 5,840,502 A | 11/1998 | Van Vlasselaer | 435/7.21 |
| 6,254,834 B1 | 7/2001 | Anderson et al. | 422/102 |
| 6,340,570 B1 | 1/2002 | Anderson et al. | 435/7.2 |
| 6,346,421 B1 | 2/2002 | Anderson et al. | 436/177 |
| 6,479,239 B1 | 11/2002 | Anderson et al. | 435/6 |
| 6,911,312 B2 | 6/2005 | Anderson et al. | 435/7.1 |
| 7,070,739 B1 | 7/2006 | Anderson et al. | 422/82.05 |
| 7,328,807 B2 | 2/2008 | Takagi et al. | 209/172.5 |
| 7,390,387 B2* | 6/2008 | Childers et al. | 204/547 |
| 7,402,131 B2* | 7/2008 | Mueth et al. | 494/36 |
| 7,802,686 B2 | 9/2010 | Takagi et al. | 209/172.5 |
| 8,087,515 B2 | 1/2012 | Kojima et al. | 209/155 |
| 8,475,730 B2* | 7/2013 | Jeong | 422/255 |
| 8,961,904 B2* | 2/2015 | Xia et al. | 422/505 |
| 2002/0127546 A1 | 9/2002 | Anderson et al. | 435/5 |
| 2002/0132230 A1 | 9/2002 | Anderson et al. | 435/5 |
| 2002/0132338 A1 | 9/2002 | Anderson et al. | 435/304.1 |
| 2002/0137026 A1 | 9/2002 | Anderson et al. | 435/5 |
| 2003/0138770 A1 | 7/2003 | Anderson et al. | 435/5 |
| 2006/0070921 A1 | 4/2006 | Takagi et al. | 209/208 |
| 2006/0275184 A1 | 12/2006 | Furukawa et al. | |
| 2008/0017553 A1 | 1/2008 | Takagi et al. | 209/172.5 |
| 2008/0160603 A1* | 7/2008 | Sundararajan et al. | 435/288.5 |
| 2010/0072112 A1* | 3/2010 | Kojima et al. | 209/39 |
| 2010/0248358 A1* | 9/2010 | Yoshioka | 435/325 |
| 2011/0036862 A1* | 2/2011 | Kanai et al. | 222/71 |
| 2011/0177547 A1* | 7/2011 | Xia et al. | 435/34 |
| 2012/0028342 A1* | 2/2012 | Ismagilov et al. | 435/283.1 |
| 2012/0091059 A1* | 4/2012 | Beer et al. | 210/634 |
| 2012/0107860 A1* | 5/2012 | Katsumoto | 435/29 |
| 2012/0202284 A1* | 8/2012 | Gal et al. | 435/325 |
| 2013/0309679 A1* | 11/2013 | Ismagilov et al. | 435/6.12 |
| 2014/0377866 A1* | 12/2014 | Haun et al. | 435/379 |

FOREIGN PATENT DOCUMENTS

| | | | |
|---|---|---|---|
| JP | 2002-505866 | 2/2002 | C12N 15/09 |
| JP | 2004-314068 | 11/2004 | B03B 5/32 |
| JP | 2005-098704 | 4/2005 | G01N 33/48 |
| JP | 2005-292092 | 10/2005 | G01N 33/48 |
| JP | 2006-116520 | 5/2006 | B03B 5/66 |
| JP | 2006-346671 | 12/2006 | |
| JP | 2007-282552 | 11/2007 | C12N 5/06 |
| JP | 2008-105010 | 5/2008 | B03B 5/32 |
| JP | 2009-168216 | 7/2009 | |
| JP | 4462058 | 2/2010 | B03B 5/66 |
| JP | 2010-75820 | 4/2010 | B03B 5/28 |
| JP | 2010-075844 | 4/2010 | |
| JP | 2011-185839 | 9/2011 | |
| JP | 2011-194379 | 10/2011 | |

OTHER PUBLICATIONS

Petersson, F., et al. (2007), "Free flow acoustophoresis: microfluidic-based mode of particle and cell separation", *Anal. Chem.*, 79(14): 5117-5123.

Sugiyama, D., et al. (2012), "Density-based particle separation using a microfluidic device", *Proceedings of the 3$^{rd}$ European Conference on Microfluidics*, 4 pages.

Sugiyama, D., et al. (2012), "Evaluation of separation based on density difference of particles in micro channel and application to cell separation", *The Society of Chemical Engineers 77$^{th}$ Annual Meeting*, p. 172—Full English Translation Provided.

Teshima, Y., et al. (2012), "Density-based particle separation using microfluidic device with mild stimulation and application of the particle separation", *25th Cheminas*, 1—Full English Translation Provided.

Teshima, Y., et al. (2012), "Density-based separation of bovine ova using microfluidic device and quality evaluation", *The Chemical Society of Japan-West Japan*, 265—Full English Translation Provided.

Teshima, Y., et al. (2012), "Microfluidic separation of bovine ova based on density difference and their quality evaluation", *Microfluidics*, 1-2.

Teshima, Y., et al. (2012), "Separation of particles based on density difference using microfluidic device and application to ova", *The Society of Chemical Engineers 44$^{th}$ Autumn Meeting*, 1 Page—Full English Translation Provided.

Teshima, Y., et al. (2012), "Density-based separation of bovine ova using microfluidic device and quality evaluation", *The Chemical Society of Japan-West Japan*, 266—Full English Translation Provided.

Sugiyama, D., et al. (2012). "Design of microfluidic device for cell sorting and separation of model particles." *The 4$^{th}$ International Symposium on Microchemistry and Microsystems*, issued on Jun. 10, 2012, presented on Jun. 12, 2012, p. 464.

Office Action issued in Japanese Patent Application No. 2012-198961 dated Mar. 15, 2016 (Japanese Only).

* cited by examiner

PARTICLE SEPARATION DEVICE AND METHOD OF SEPARATING PARTICLES

This Nonprovisional application claims priority under 35 U.S.C. §119(a) on Patent Application No. 2012-198961 filed in Japan on Sep. 10, 2012, the entire contents of which are hereby incorporated by reference.

TECHNICAL FIELD

The present invention relates to a particle separation device and a method of separating particles. More specifically, the present invention relates to a particle separation device and a method of separating particles, each of which (i) includes a flow path of micrometer order and (i) separates, in accordance with a difference in density, a particle group whose particles (such as cells and chemically synthesized particles) are different in density.

BACKGROUND ART

There are known various methods of separating a particle group whose particles (such as cells and chemically synthesized particles) are different in properties, for example, a method of separating a particle group on the basis of a difference in mass, a method based on a size of particles, and a method based on a difference in density.

Methods, such as a sedimentation equilibrium method and a sedimentation velocity method with use of a separation fluid whose density is regulated and a centrifugal separation method, are exemplified as a method of separating, in accordance with a difference in density, a particle group whose particles are different in density (see Patent Literature 1 through 6).

In a case where cells are separated as particles, there is a known method in which (i) magnetic particles or fluorescent molecules are attached to cells by using a specific antigen-antibody reaction which is an inherent immunological property of a biospecimen such as cells and (ii) the cells are separated by a cell separation device such as a magnetic cell sorter or a fluorescence-activated cell sorter.

Further, there is studied another method in which electrophoresis or a flocculant is used in a micro flow path (see Patent Literature 7). Furthermore, there have been developed a device for separating a particle group in a micro flow path on the basis of a density with use of an ultrasonic wave or a pinched flow path (see Non-Patent Literatures 1, 2) and another method of classifying a minute particle group (see Patent Literatures 8, 9).

CITATION LIST

Patent Literatures

Patent Literature 1
Japanese Translation of PCT International Application Tokuhyohei No. 10-508190 A (Publication date: Aug. 18, 1998)
Patent Literature 2
Japanese Translation of PCT International Application Tokuhyo No. 2002-505866 A (Publication date: Feb. 26, 2002)
Patent Literature 3
Japanese Patent Application Publication, Tokukai, No. 2007-282552 A (Publication date: Nov. 1, 2007)
Patent Literature 4
Japanese Patent Application Publication, Tokukai, No. 2008-105010 A (Publication date: May 8, 2008)
Patent Literature 5
Japanese Patent Application Publication, Tokukai, No. 2005-98704 A (Publication date: Apr. 14, 2005)
Patent Literature 6
Japanese Patent Application Publication, Tokukai, No. 2004-314068 A (Publication date: Nov. 11, 2004)
Patent Literature 7
Japanese Patent Application Publication, Tokukai, No. 2005-292092 A (Publication date: Oct. 20, 2005)
Patent Literature 8
JP patent No. 4462058 (Registration date: Feb. 26, 2010)
Patent Literature 9
Japanese Patent Application Publication, Tokukai, No. 2010-75820 A (Publication date: Apr. 8, 2010)

Non-Patent Literatures

Non-Patent Literature 1
Anal Chem, 2007 Jul. 15; 79(14) p 5117-5123
Non-Patent Literature 2
Microfluid Nanofluid, 2011 Mar. 8; 11 p 105-110

SUMMARY OF INVENTION

Technical Problem

However, in a case where the sedimentation equilibrium method, the sedimentation velocity method, or the centrifugal separation method as described above is used, target particles are gathered by pipetting when separated particles are collected. At this time, particle groups are necessarily kept away from each other in order to prevent contamination of particles. Because of this, the particles need a long travel distance. For example, in a case of the centrifugal separation method, it is necessary to carry out centrifugation for a long time with a stronger centrifugal force.

In a case where, for example, somatic cells are used as particles, the somatic cells undergo a great stress. Therefore, in researches with use of somatic cells, there often arise a problem that a cell function of somatic cells is reduced and a problem that a cell response of somatic cells cannot be observed enough. There is also another problem that complicated operations are required when separated particles are collected, so that it takes much effort and a long time.

Meanwhile, in a case of a method with use of a cell separation device, an advanced skill and complicated operation are required, so that it much effort and a long time.

In a case of the method in which electrophoresis or a flocculant is used in a micro flow path and a method with use of an ultrasonic wave or a pinched flow path in a micro flow path, the following problem arises. Specifically, the method disclosed in Patent Literature 7 is a method in which cells are separated by using a difference in viscosity, so that the method is not suitably used for separating cells whose densities are close to each other. Furthermore, a method disclosed in Non-Patent Literature 1 is the method of classifying particles in view of a size and a density of the particles with use of an ultrasonic wave, so that the method causes somatic cells to undergo a great stress. A method disclosed in Non-Patent Literature 2 is a method of separating particles in view of a size and a density of the particles, however, the method is not accurate enough. Still further, methods disclosed in Patent Literatures 8 and 9 are not designed for particles (e.g., cells) which are identical in size but different in other properties such as density, so that the method cannot separate the particles.

For these reasons, there is demanded an easy method of separating and collecting a particle group, which includes particles that are identical in particle diameter (size) but different in other properties such as a density, for a short time with less stimulation.

The present invention has been made in view of the above problems, and an object of the present invention is mainly to provide a particle separation device and a method of separating particles, each of which can easily separate a particle group for a short time without a great stress such as a gravity load to particles and easily collect the particle group thus separated.

Solution to Problem

As a result of diligently examination to achieve the above object, the inventors of the present invention focused on a point that particle groups of somatic cells and chemically synthesized particles which are different in particle diameter or density were differently moved in a fluid in accordance with the Stokes' formula, and considered that those particle groups could be separated in a flow path in which a separation fluid was flown. Accordingly, the inventors have achieved a particle separation device and a method of separating particles in accordance with the present invention.

That is, in order to achieve the above object, a particle separation device in accordance with the present invention includes at least: a separation flow path (i) to which a separation fluid and a particle group including two types of particles being different in density are supplied, and (ii) through which the separation fluid flows in a certain direction; a divergence section connected to at least an end of the separation flow path in the certain direction in which the separation fluid flows, a first flow path formed from the divergence section in a rising direction; and a second flow path formed from the divergence section in a falling direction, the separation flow path being formed in a horizontal direction. Note that, the term 'falling direction' means a 'direction of gravity', and the term 'rising direction' means a 'direction against gravity'.

Further, in order to achieve the above object, a method of separating particles in accordance with the present invention with use of the particle separation device includes the step of separating a particle group into a particle group having a high density and a particle group having a low density.

Advantageous Effects of Invention

According to the particle separation device and the method of separating particles of the present invention, in accordance with the Stokes' formula, a particle group having a higher density is flown in a region in a relatively falling direction of a separation flow path through which a separation fluid is flown in a certain direction, meanwhile, a particle group having a lower density is flown in a region in a relatively rising direction of the separation flow path. In other words, the particle groups differently move in the direction of gravity in accordance with the difference in density. It is therefore possible to separate and collect the particle groups which are identical in particle diameter (size) but different in difference in density. This makes it possible to easily separate a particle group for a short time without a great stress such as a gravity load to particles and easily collect the particle group thus separated.

BRIEF DESCRIPTION OF DRAWINGS (a) of FIG. 1 is a side view illustrating a schematic structure of a particle separation device in Example 1 in accordance with one embodiment, and (b) of FIG. 1 is a cross-sectional view taken along the line X-X' of (a) of FIG. 1.

(a) of FIG. 2 and (b) of FIG. 2 are both side views each in which a divergence section and a periphery of the divergence section of the particle separation device for use in a separation evaluation test of Example 1 are observed in a horizontal direction.

(a) of FIG. 3 is a plan view illustrating a schematic structure of a particle separation device of Example 2 in accordance with one embodiment. (b) of FIG. 3 is a cross-sectional view taken along the line Y-Y' of (a) of FIG. 3. (c) of FIG. 3 is a cross-sectional view taken along the line Y"-Y'" of (a) of FIG. 3.

(a) of FIG. 4 is a plan view in which a divergence section and a periphery of the divergence section of the particle separation device for use in a separation evaluation test of Example 2 are observed in a vertical direction. (b) of FIG. 4 corresponds to (a) of FIG. 4 and is a schematic cross-sectional view seen in a horizontal direction.

(a) of FIG. 5 is a plan view in which a divergence section and a periphery of the divergence section of the particle separation device to be subjected to the separation evaluation test of Example 2 are observed in a vertical direction. (b) of FIG. 5 corresponds to (a) of FIG. 4 and is a schematic cross-sectional view seen in a horizontal direction.

(a) of FIG. 6 is a plan view illustrating a schematic structure of a particle separation device in Example 3 in accordance with one embodiment. (b) of FIG. 6 is a cross-sectional view taken along the line Z-Z' of (a) of FIG. 6. (c) of FIG. 6 is a cross-sectional view taken along the line Z"-Z'" of (a) of FIG. 6.

(a) of FIG. 7 is a plan view in which a divergence section and a periphery of the divergence section of the particle separation device for use in a separation evaluation test of Example 3 are observed in a vertical direction. (b) of FIG. 7 corresponds to (a) of FIG. 7 and is a schematic cross-sectional view seen in a horizontal direction.

FIG. 8 is an explanatory view to explain how particles move in a separation flow path in accordance with the Stokes' formula.

(a) to (c) of FIG. 9 illustrate modification examples of a particle separation device in another embodiment, each of which is an explanatory view to explain a schematic structure of the particle separation device.

(a) of FIG. 10 is a plan view illustrating a schematic structure of a particle separation device in Example 6 in accordance with one embodiment. (b) of FIG. 10 is a cross-sectional view taken along the line $W_1$-$W_2$ of (a) of FIG. 10. (c) of FIG. 10 is a cross-sectional view taken along the line $W_3$-$W_4$ of (a) of FIG. 10. (d) of FIG. 10 is a cross-sectional view taken along the line $W_5$-$W_6$ of (a) of FIG. 10. (e) of FIG. 10 is a cross-sectional view taken along the line $W_7$-$W_8$ of (a) of FIG. 10.

Figure 13:
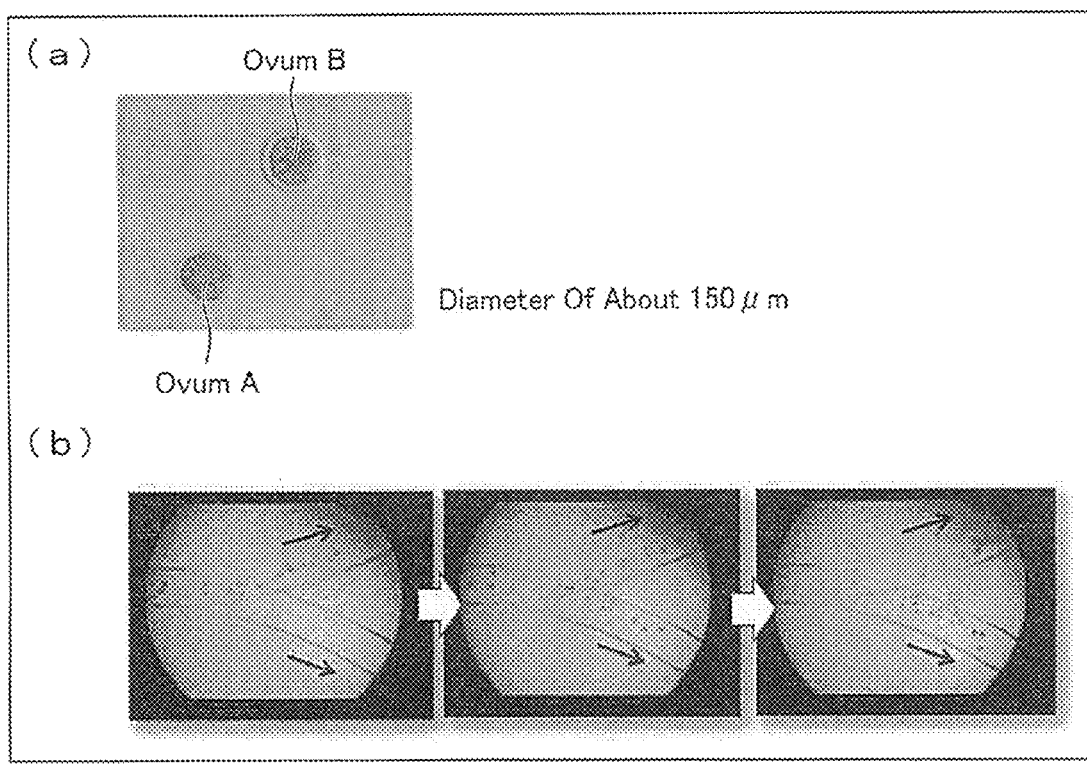

(a) of FIG. 13 is a plan view in which a low-quality ovum A and a medium-quality to high-quality ovum B in Example 6 are observed in a vertical direction, and (b) of FIG. 13 is a plan view in which a divergence section and the periphery of the divergence section of a particle separation device to be subjected to a separation evaluation test of Example 6 are observed in a vertical direction.

DESCRIPTION OF EMBODIMENTS

In the following description, the term 'density' indicates 'density at a temperature of 25° C.'. In the drawings, 'g' indicates a direction of gravity.

Embodiment 1

Figure 1:
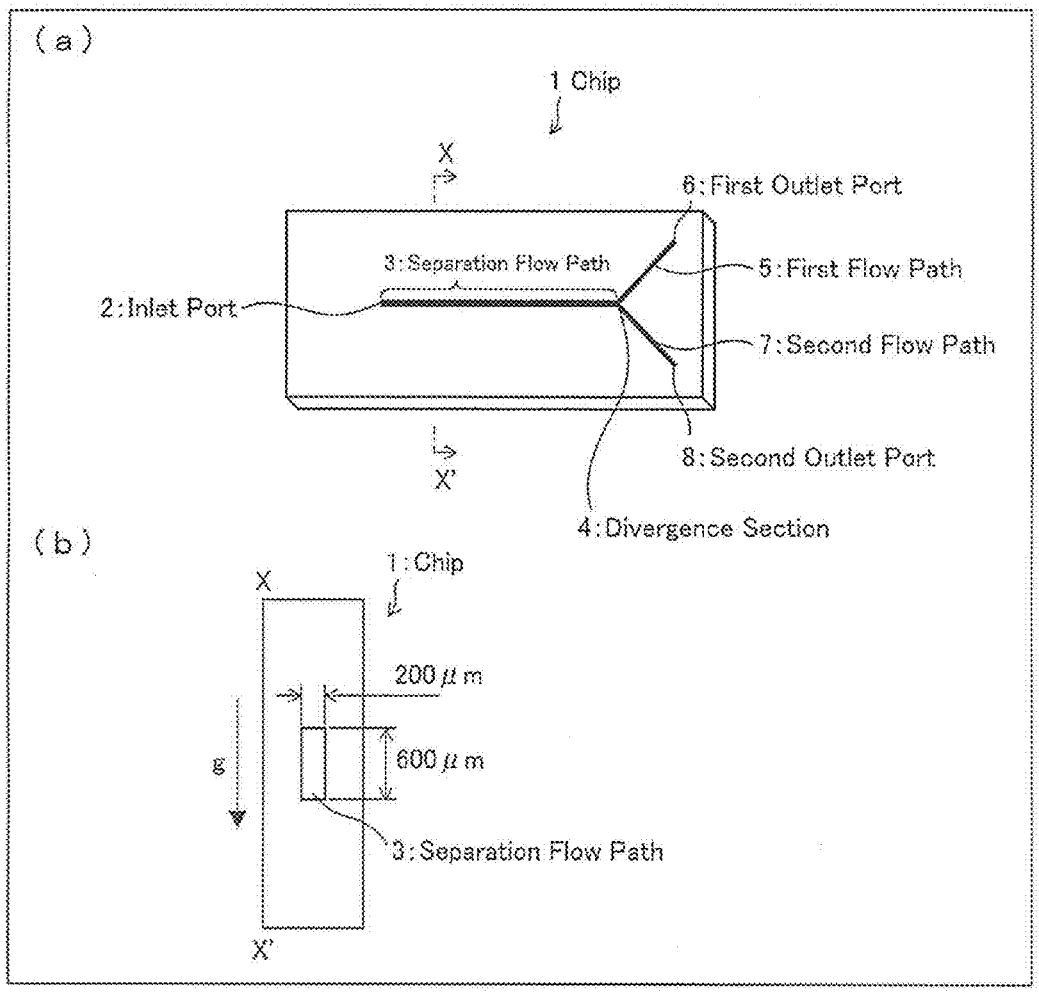

The following description will discuss one embodiment of the present invention with reference to the drawings. (a) of FIG. 1 is a side view illustrating a schematic structure of a particle separation device in Example 1 (described later), and (b) of FIG. 1 is a cross-sectional view taken along the line X-X' of (a) of FIG. 1. The particle separation device of Embodiment 1 includes a chip 1 which is a main part of the particle separation device as shown in (a) of FIG. 1, and the chip 1 includes at least an inlet port 2, a separation flow path 3, a divergence section 4, a first flow path 5, a first outlet port 6, a second flow path 7, and a second outlet port 8.

The chip 1 is made from, for example, a metal or resin. The metal or the resin which can be used for the chip 1 is not particularly limited unless particles to be separated adhere to the metal or the resin or the metal or the resin is dissolved or changed by a separation fluid. The resin may be or may not be transparent. Specific examples of the resin encompass polydimethylsiloxane (PDMS). The chip 1 may have any shape such as a rectangular shape as shown in (a) of FIG. 1, a disk shape, a triangular shape, a quadrangular shape with a parallelogram undersurface, or an indeterminate shape.

The inlet port 2 is for introducing a separation fluid containing a particle group into the separation flow path 3. A size or shape of the inlet port 2 may be determined in accordance with those of the separation flow path 3. For example, the inlet port 2 has such a shape as to fix, for example, a fluid-feeding tube for introducing a separation fluid containing a particle group from the outside. Further, the inlet port 2 may have a size smaller than that of the separation flow path 3 or may provide a throttle so that a particle group can be emitted from a single point into the separation flow path 3.

The separation flow path 3 is for separating a particle group, which is contained in a separation fluid, on the basis of a particle diameter and a difference in density between particles of the particle group and a separation fluid in accordance with the following formula (1) (Stokes' formula). A particle group in a separation fluid sediments in the direction of gravity or rising in the direction against gravity at a certain velocity in accordance with formula (1) (Stokes' formula) below while being flown through the separation flow path 3 in a certain direction. In theory, a particle does not rise or sediment if a density of the particle is equal to that of the separation fluid.

[Math. 1]

$$y_s = \frac{DP^2(\rho_p - \rho_f)g}{18\eta} \quad (1)$$

(where, in the formula (1), $v_s$ represents a theoretical rising velocity or a theoretical sedimentation velocity of each particle in the divergence section 4, Dp represents a particle diameter of each particle, $\rho_p$ represents a density of each particle, $\rho_f$ represents a density of a separation fluid, g represents a gravitational acceleration, and $\eta$ represents a viscosity of the separation fluid.)

Figure 8:
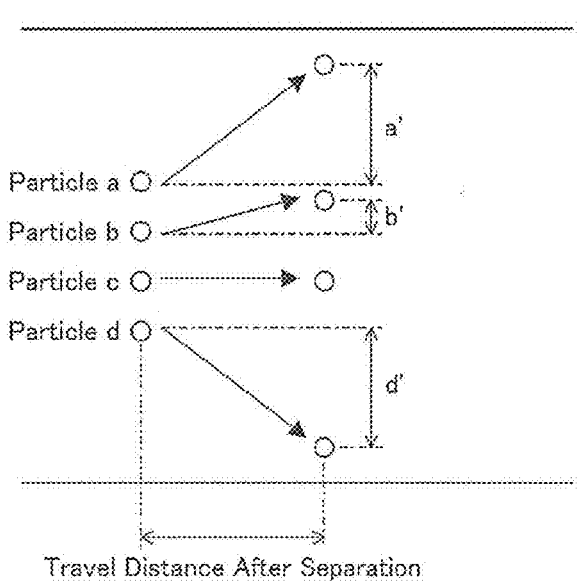

The formula (1) will be theoretically described with reference to FIG. 8. A particle a, a particle b, a particle c, and a particle d shown in FIG. 8 are assumed that the particle d has the highest density, and the particle c, the particle b, and the particle a have the second highest density, the third highest density, and the lowest density, respectively. Further, the particle c is assumed to have a density equal to that of s separation fluid. In this case, the particle a rises because the particle a has the lowest density (minimum density) and therefore has a fastest rising velocity. Although a rising velocity of the particle b is slower than that of the particle a, the particle b having the second lowest density also rises. The particle c whose density is equal to that of the separation fluid does not rise or sediment. The particle d whose density is the highest (maximum density) sediments.

As a result, as shown in FIG. 8, the particles a through d sediment or rise along with flow in the separation flow path 3. That is, the particles a to d are theoretically rise or sediment while moving like a linear shape. Then, a distance a' at which the particle a rises in the direction against gravity is larger than a distance b' at which the particle b rises. Further, the particle d sediments a distance of d' in the direction of gravity.

That is, in the chip 1, a length and a flow path diameter of the separation flow path 3, and a density, a viscosity, and a flow rate of the separation fluid may be optimally set in accordance with the above formula (1) on the basis of particle diameters or densities of particles of a particle group to be separated.

For example, a particle group rises or sediments a distance of 450 μm in the direction of gravity (or in the direction against gravity) in a case where (I) the separation flow path 3 is horizontal to gravity, (II) a particle group contains two kinds of particles: particles that have a low density which is lower than that of a separation fluid by 0.002 g/mL; and particles that have a high density which is higher than that of the separation fluid by 0.002 g/mL, (III) the following conditions are satisfied: (a) the separation fluid has a linear velocity of 7 cm/min in the separation flow path 3, (b) the separation fluid has a flow rate of 20 μL/min, (c) the separation fluid has a viscosity of 0.0018 kg/(m·s), (d) each particle has a particle diameter of 150 μm, and (e) a residence time is 30 seconds. With this, in a case where a particle group is introduced into the separation flow path 3 even at random, all particles can rise or sediment if the flow path diameter of the separation flow path 3 is set to 450 μm or less in the direction of gravity. In a case where a particle group is introduced into a single point of the separation flow path 3, it is found that the particle group rises or sediments in the direction of gravity (or the direction against gravity) at a distance of about 450 μm from the certain point.

The separation flow path 3 may be tilted at a certain degree. A tilt angle may be determined on the basis of a flow rate of a separation fluid, a flow path diameter of the separation flow path 3, and the like. Specifically, assuming that the horizontal direction is 0 deg., a tilt angle of the separation flow path 3 falls preferably within the range of −30 deg. to 30 deg., more preferably within the range of −15 deg. to 15 deg., and further more preferably within the range of −5 deg. to 5 deg.

A cross-sectional shape of the separation flow path 3 is not limited to a rectangular shape shown in (b) of FIG. 1, and may be a square, a circle, or an oval. The flow path diameter (minimum diameter) of the separation flow path 3 is preferably three or more times, more preferably five or more times, and further more preferably ten or more times as large as particle diameters of particles of a particle group to be separated. The larger the flow path diameter is with respect to the particle diameters, the better. This reduces a possibility that the separation flow path 3 is clogged with the particle group. Note, however, that, in order not to cause the chip 1 to become too large, it is preferable that the flow path diameter (minimum diameter) of the separation flow path 3 be 1,000 or less times as large as a particle diameters of the particles of the particle group. Similarly, flow path diameters (minimum diameters) of the divergence section 4, the first flow path 5, and the second flow path 7 are preferably three or more times, more preferably five or more times, and further more preferably ten times as large as the particle diameters of the particles of the particle group to be separated.

Specifically, a flow path diameter (maximum diameter) of the separation flow path 3 is preferably 100,000 μm or less, more preferably 10,000 μm or less, and further more preferably 1,000 μm or less. If the flow path diameter is too large, it may be difficult to carry out separation, which may result in reduction of the separation efficiency. Further, specifically, the flow path diameter (minimum diameter) of the separation flow path 3 is preferably 1 μm or more, more preferably 10 μm or more, and further more preferably 100 μm or more. If the flow path diameter is too small, the separation flow path 3 may be clogged with the particle group.

Although a length of the separation flow path 3 may be set in accordance with a particle group to be separated, specifically, the length falls preferably within the range of 0.1 cm to 100 cm, and more preferably within the range of 1 cm to 10 cm. If the separation flow path 3 is too short, separation may be carried out inaccurately, which may result in contamination. On the contrary, if the separation flow path 3 is too long, efficiency of separation is reduced.

The divergence section 4 is connected to the separation flow path 3, and has a divergence point that causes a separation fluid, which contains a particle group distributed in the direction of gravity in accordance with the formula (1), to be separated at least at an end of the separation flow path 3 into (a) the first flow path 5 extending toward a rising direction (direction against gravity) and (b) the second flow path 7 extending toward a falling direction (direction of gravity). A structure of the divergence section 4 is, for example, a vertical Y structure (structure of FIG. 1), however, the structure is not limited thereto. Other examples of the divergence section 4 encompass a vertical T structure, a double-layer structure, and a plane double-layer Y structure (structure of FIG. 3). The vertical Y structure is a structure in which two flow paths are branched from the separation flow path 3 in the vertical direction so as to form a shape of Y, and is a structure which can efficiently separate particles in a case where a particle group to be separated is a mixture of sedimenting particles and rising particles. In a case where the particle separation device of Embodiment 1 is used, a maximum surface of the chip 1 is fixed in substantially vertical direction with respect to the direction of gravity. The wording "substantially vertical direction" includes not only the vertical direction but also a direction tilted at a certain degree. For example, in a case where the maximum surface of the chip 1 which is vertically provided is 90 deg., the tilt angle may fall within the range of 60 deg. to 120 deg., and more preferably within the range of 70 deg. to 110 deg. If the tilt angle is too small or too large, accuracy of separation may be reduced.

The vertical T structure is similar to the vertical Y structure other than a point that two flow paths are branched from the separation flow path 3 in the vertical direction so as to form a shape of T. The double-layer structure is a structure in which two layers are stacked to be in parallel with the maximum surface of the chip 1. With the double-layer structure, it is possible to use the chip 1 while fixing the maximum surface of the chip 1 in the direction horizontal to gravity. The plane double-layer Y structure is similar to the double-layer structure other than a point that the first flow path 5 and the second flow path 7, which are provided in two layers, respectively, are branched so as to form the shape of Y while being in parallel to the maximum surface of the chip 1.

The first flow path 5 is a flow path extending toward the rising direction (direction against gravity) of the divergence section 4. In the separation flow path 3, a particle group having a low density (particles having a density lower than that of the separation fluid) rises and is distributed in the rising direction in the separation fluid which flows from the separation flow path 3 toward the divergence section 4 (in a certain direction). Therefore, the separation fluid, which contains the particle group having the low density, is separated at the divergence section 4 to be supplied to the first flow path 5 which is formed in the rising direction. That is, the first flow path 5 allows the separation fluid which contains the particle group having the low density to pass.

A shape of the first flow path 5 may be a rectangular shape, and may be a square, a circle, an oval, or an indeterminate shape. Specifically, a flow path diameter (maximum diameter) of the first flow path 5 is preferably 100,000 μm or less, more preferably 10,000 μm or less, further more preferably 1,000 μm or less. Further, specifically, a flow path diameter (minimum diameter) of the first flow path 5 is preferably 1 μm or more, more preferably 10 μm or more, further more preferably 100 μm or more. If the flow path diameter is too small, the first flow path 5 may be clogged with a particle group. Further, a length of the first flow path 5 is not particularly limited.

A cross-sectional area of the first flow path 5 is not particularly limited, but it is preferable that a total cross-sectional area of the first flow path 5 and the second flow path 7 (described below) be equal to or less than a cross-sectional area of the separation flow path 3 in order to prevent a separation fluid from being resident or flown backward.

The first outlet port 6 is for discharging a separation fluid, which has been separated in the chip 1, containing a particle group having a low density. A size and a shape of the first outlet port 6 may be determined in accordance with those of the first flow path 5. The first outlet port 6 may be shaped to fix, for example, a fluid-feeding tube for collecting a separation fluid containing a particle group which has been separated in the chip 1. Alternatively, the first outlet port 6 may be shaped to provide a pool for collecting a separation fluid containing a particle group which has been separated in the chip 1.

The second flow path 7 is a flow path extending toward the falling direction (direction in gravity) of the divergence section 4. In the separation flow path 3, a particle group having a high density (particles having a density higher than that of a separation fluid) sediments and is distributed in the falling direction in the separation fluid which flows from the separation flow path 3 toward the divergence section 4 (in a certain direction). Therefore, a separation fluid, which contains the particle group having the high density, is separated at the divergence section 4 to be supplied to the second flow path 7 which is formed in the falling direction. That is, the second flow path 7 allows the separation fluid which contains the particle group having the high density to pass.

A shape and a flow path diameter (minimum diameter) of the second flow path 7 may be similar to those of the first flow path 5. Note, however, that the first flow path 5 and the second flow path 7 have different structures, and, for example, the flow path diameter (minimum diameter) of the first flow path 5 may be small and the flow path diameter (minimum diameter) of the second flow path 7 may be large in accordance with a particle diameter.

The second outlet port 8 is for discharging a separation fluid, which has been separated in the chip 1, containing a particle group which has a high density. The size and the shape of the second outlet port 8 may be determined in accordance with those of the second flow path 7. The shape of the second outlet port 8 may be shaped to fix, for example, a fluid-feeding tube for collecting a separation fluid containing a particle group which has been separated in the chip 1. Alternatively, the shape of the second outlet port 8 may be shaped to provide a pool for collecting a separation fluid containing a particle group which has been separated in the chip 1.

The chip 1, which is a main part of the particle separation device in accordance with the present invention, can be more simply formed in such a way that, for example, (i) a first member, in which grooves for constituting the separation flow path 3 which is a micro flow path (a flow path of micrometer order), the divergence section 4, the first flow path 5, and the second flow path 7, are made, and (ii) a second member, in which grooves for constituting the separation flow path 3, the divergence section 4, the first flow path 5, and the second flow path 7 are made, are stacked on each other so that the grooves of the first member and the corresponding grooves of the second member constitute the separation flow path 3, divergence section 4, the first flow path 5, and the second flow path 7. Further, by forming the chip 1 as described above, the separation flow path 3, the divergence section 4, the first flow path 5, and the second flow path 7 can be cleaned more easily.

Further, the chip 1, which is a main part of the particle separation device in accordance with the present invention, can be more simply formed in such a manner that, for example, (i) a first member, in which grooves for constituting the separation flow path 3 which is a micro flow path, the divergence section 4, and the first flow path 5 are made, and (ii) a second member, in which grooves for constituting the separation flow path 3, the divergence section 4, and the second flow path 7 are made, are stacked on each other so that the grooves of the first member and the corresponding grooves of the second member constitute the separation flow path 3, the divergence section 4, the first flow path 5, and the second flow path 7. Further, by forming the chip 1 as described above, the separation flow path 3, the divergence section 4, the first flow path 5, and the second flow path 7 can be cleaned more easily. Furthermore, with the above structure (structure of FIG. 3), the first flow path 5 and the second flow path 7 can be formed on different sides (i.e., can be formed to have a double-layer structure) seen from the separation flow path 3. This makes it possible to make smaller a width (height) of the chip 1 of the particle separation device in the vertical direction.

Furthermore, the chip 1, which is a main part of the particle separation device in accordance with the present invention, can be more simply formed in such a manner that, for example, (i) a first member, in which grooves for constituting the separation flow path 3 which is a micro flow path (a flow path of micrometer order), the divergence section 4, the first flow path 5, and the second flow path 7 are made, and (ii) a flat second member, in which no groove is made, are stacked on each other so that the grooves constitute the separation flow path 3, the divergence section 4, the first flow path 5, and the second flow path 7. Further, by forming the chip 1 as described above, the separation flow path 3, the divergence section 4, the first flow path 5, and the second flow path 7 can be cleaned more easily.

A separation fluid to be supplied to the separation flow path 3 of the particle separation device can be any fluid provided that the separation fluid allows particles of a particle group to be dispersed or suspended. Specifically, the separation fluid may be, for example, water or an organic solvent, and is not particularly limited provided that the separation fluid does not dissolve or change quality of particles to be separated, or does not dissolve or change quality of the chip 1 in which the separation flow path 3, the divergence section 4, the first flow path 5, and the second flow path 7 are made. Further, a density and a viscosity of the separation fluid may be appropriately changed on the basis of the formula (1) in accordance with a density and a particle diameter of each particle of a particle group to be separated, and a flow path diameter and a length of a flow path of the separation flow path 3 etc. In order to change the density and the viscosity of the separation fluid, for example, an organic compound such as a salt or a saccharide, which does not change quality of particles, may be dissolved in advance.

A separation fluid passes through the separation flow path 3, the divergence section 4, the first flow path 5, and the second flow path 7 in a laminar flow. That is, the separation fluid passes through the chip 1 in a laminar flow. Therefore, a particle group is moved in accordance with the formula (1).

A particle group, which is a target to be separated in the present invention, can be any particle group provided that the particle group stably exists in a separation fluid, and examples of the particle group encompass a particle group of bioparticles, a particle group of resin particles, and a particle group of metal particles. Examples of the bioparticles encompass somatic cells including ova, erythrocytes, platelets, bacteria, yeast fungi, cell fractions, lipid particles, protein micelles, planktons, and algae, each of which are particles that hardly move. For example, the present invention makes it possible to separate a fertilized egg and an unfertilized egg which are different in density. Examples of the resin particles encompass a particle group of organic high-molecules and a particle group of inorganic high-molecules. Examples of the metal particles encompass particle-like alloy, iron sand, and gold dust. Those particles preferably have a spherical shape, but may have a substantially spherical shape, an ovally spherical shape, or an indeterminate crushed shape.

The particles are required to have a particle diameter of 0.1 µm or more, preferably 1 µm or more, and more preferably 10 µm or more. If the particle diameter of the particles is too small, the particles do not satisfy the formula (1) and a rising velocity or a sedimentation velocity of the particles becomes extremely slow. Therefore, it is necessary to extremely extend the separation flow path 3. This results in upsize of the particle separation device. In addition, a ratio of particles which are not separated to particles collected from the first outlet port 6 or the second outlet port 8 is increased in some cases.

The particles are required to have a particle diameter of 5,000 µm or less, preferably 1,000 µm or less, and more preferably 100 µm or less. If the particle diameter of the particles is too large, the particles do not satisfy the formula (1), and the rising velocity or the sedimentation velocity of the particles becomes extremely fast. Therefore, in a case where a separation fluid is slowly flown, the separation flow path 3 may be clogged with the particles. In addition, it might be difficult to accurately separate particles with ease.

A minimum difference in density between a particle to be separated into the first flow path 5 and a particle to be separated into the second flow path 7 is not particularly limited, but is required to be 0.001 g/mL or more, preferably 0.002 g/mL or more, more preferably 0.005 g/mL or more, and particularly preferably 0.01 g/mL or more. This makes it possible to prevent contamination of separated particles, so that particles can be separated more accurately.

That is, with the above structure, the particle separation device in accordance with Embodiment 1 can prevent contamination of separated particles, thereby separating particles more accurately.

The particle separation device may include, in addition to the chip 1 which is a main part, a liquid-feeding device such as a syringe pump for supplying a separation fluid, a stirring device such as a stirrer or a vortex mixer for stirring a separation fluid containing a particle group, a fluid-feeding tube made from silicone or the like, a water tank, a suction device, as necessary. In other words, the particle separation device may cause a liquid-feeding device to stir a separation fluid containing a particle group to thereby suspend the separation fluid, and supply the separation fluid to the separation flow path 3 of the chip 1 from the inlet port 2 through a fluid-feeding tube with use of the liquid-feeding device. As an alternative, the particle separation device may supply a separation fluid containing a particle group to the separation flow path 3 of the chip 1 from the inlet port 2 through a fluid-feeding tube or the like while suspending the separation fluid by using a difference in gravity from a high position. As another alternative, it is also possible to supply a separation fluid containing a particle group to the separation flow path 3 by sucking the separation fluid from the first outlet port 6 and the second outlet port 8 with use of a suction device. As another alternative, a separation fluid containing a particle group discharged from the first outlet port 6 or the second outlet port 8 may be collected to a water tank through a fluid-feeding tube or the like. It is also possible to collect a separation fluid containing a particle group to a water tank by sucking the separation fluid from the first outlet port 6 and the second outlet port 8 through fluid-feeding tubes with use of a suction device.

In order to separate a particle group from a separation fluid containing the particle group discharged from the first outlet port 6 or the second outlet port 8, the separation fluid may be filtered or sedimented, for example.

Therefore, the present invention also provide a method of separating a particle group into particle group having a high density and a particle group having a low density with use of the particle separation device.

Embodiment 2

Figure 3:
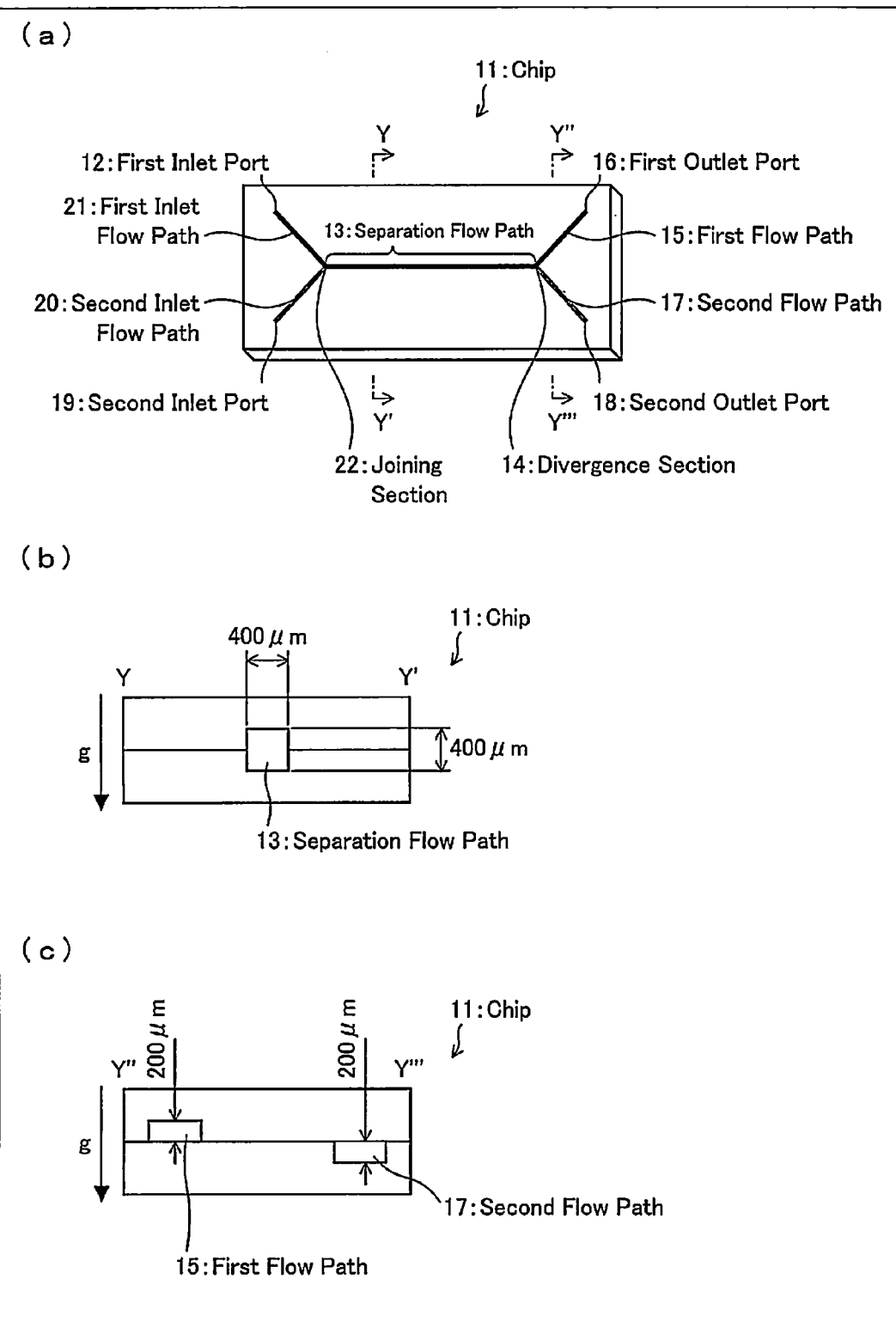

Another embodiment of the present invention will be described below with reference to drawings. (a) of FIG. 3 is a plan view illustrating a schematic structure of a particle separation device of Example 2 (described below). (b) of FIG. 3 is a cross-sectional view taken along the line Y-Y' of (a) of FIG. 3. (c) of FIG. 3 is a cross-sectional view taken along the line Y"-Y'" of (a) of FIG. 3. A particle separation device in accordance with Embodiment 2 includes a chip 11, which is a main part of the particle separation device, as shown in (a) of FIG. 3. The chip 11 includes at least a first inlet port 12, a first inlet flow path 21, a second inlet port 19, a second inlet flow path 20, a joining section 22, a separation flow path 13, a divergence section 14, a first flow path 15, a first outlet port 16, second flow path 17, and a second outlet port 18.

Note that the chip 11 corresponds to the chip 1 of Embodiment 1, the first inlet port 12 and the second inlet port 19 correspond to the inlet port 2, the separation flow path 13 corresponds to the separation flow path 3, the first flow path 15 corresponds to the first flow path 5, the first outlet port 16 corresponds to the first outlet port 6, the second flow path 17 corresponds to the second flow path 7, and the second outlet port 18 corresponds to the second flow path 8. Therefore, structures or forms which are not particularly described in the following description are similar to those of Embodiment 1.

The first inlet port 12 and the second inlet port 19 are for introducing a separation fluid containing a particle group into the first inlet flow path 21 and the second inlet flow path 20, respectively. Sizes and shapes of the first inlet port and the second inlet port 19 may be determined in accordance with those of the first inlet flow path 21 and the second inlet flow path 20, respectively. For example, like the shape of the inlet port 2 of Embodiment 1, the first inlet flow path 21 and the second inlet flow path 20 have such a shape as to fix, for example, a fluid-feeding tube for introducing a separation fluid containing a particle group from the outside. Further, the first inlet port 12 and the second inlet port 19 may have a size smaller than that of the separation flow path 13 or may provide a throttle so that the particle group can be emitted from a single point into the separation flow path 13.

A particle group contained in a separation fluid supplied from the first inlet port 12 may be different from that supplied from the second inlet port 19. Alternatively, a separation fluid containing a particle group may be supplied from one inlet port, and a buffer solution or a separation fluid having a different density may be supplied from another inlet port. The buffer solution is introduced to maintain a separation fluid containing a particle group at a certain density, or stably maintain a particles. By supplying the separation fluid having the different density, it is possible to produce, in the separation flow path 13, a separation fluid (mixed solution) having a specified density which is different from that of the separation fluid containing the particle group. In other words, it is possible to adjust a density of a separation fluid so as to suitably separate particles in accordance with the formula (1).

The first inlet flow path 21 and the second inlet flow path 20 are tubes for feeding a separation fluid containing a particle group from the first inlet port 12 and the second inlet port 19, respectively, to the joining section 22. Flow path diameters (maximum diameters) of the first inlet flow path 21 and the second inlet flow path 20 are required to be identical to the flow path diameter (maximum diameter) of the separation flow path 13. Specifically, the flow path diameters are preferably 50,000 µm or less, more preferably 5,000 µm or less, and more preferably 500 µm or less. Further, specifically, flow path diameters (minimum diameters) of the first inlet port 12 and the second inlet port 19 are preferably 1 µm or more, more preferably 10 µm or more, and further more preferably 100 µm or more.

If the flow path diameter (minimum diameter) is too small, the first inlet flow path 21 and the second inlet flow path 20 may be clogged with a particle group. The flow path diameters of the first inlet flow path 21 and the second inlet flow path 20 may be different from each other. Further, a total cross-sectional area of the first inlet flow path 21 and the second inlet flow path 20 is not particularly limited, but is preferably smaller than a cross-sectional area of the separation flow path 13 in order to prevent a separation fluid from being resident or flowing backward.

The joining section 22 has a joining point at which the first inlet flow path 21 and the second inlet flow path 20 join. A structure of the joining section 22 is required to be similar to that of the divergence section 4 of Embodiment 1, and, is, for example, a plane Y structure (structure of the divergence section 4 of FIG. 1), a plane T structure, a double-layer structure, or a plane double-layer Y structure (structure of FIG. 3). In order to efficiently mix a separation fluid with a buffer solution or to efficiently mix separation fluids being different in density with each other, which are flown from the first inlet flow path 21 and the second inlet flow path 20, a part of the joining section 22 becomes gradually narrowed and then gradually widened. Alternatively, the joining section 22 may have a throttle structure.

Like the separation flow path 3 of Embodiment 1, the separation flow path 13 is for separating particles contained in a separation fluid on the basis of a difference in density between particle diameters or between separation fluids in accordance with the formula (1). Therefore, in the chip 11, a length and a flow path diameter of the separation flow path 13, and a density, a viscosity, and a flow rate of a separation fluid can be optimally set in accordance with the above formula (1) on the basis of particle diameters or density of a particle group to be separated.

The divergence section 14 is formed as the plane double-layer Y structure in FIG. 3, however, is not limited thereto like the divergence section 4 of Embodiment 1.

That is, with the above structure, the particle separation device in accordance with Embodiment 2 can prevent contamination of separated particles, thereby separating particles more accurately.

Embodiment 3

Figure 6:
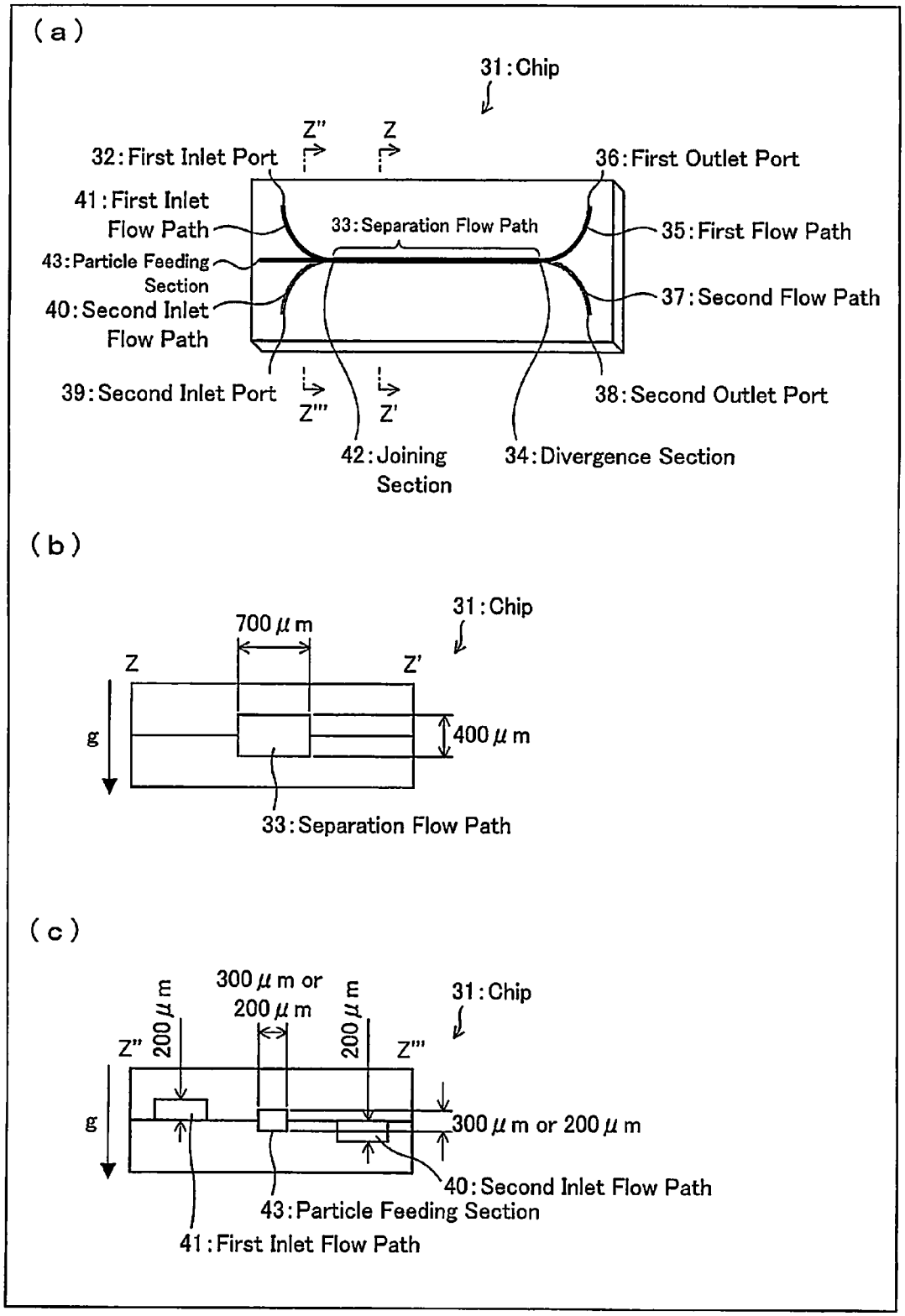

Still another embodiment of the present invention will be described below with reference to drawings. (a) of FIG. 6 is a plan view illustrating a schematic structure of a particle separation device in Example 3 (described below). (b) of FIG. 6 is a cross-sectional view taken along the line Z-Z' of (a) of FIG. 6. (c) of FIG. 6 is a cross-sectional view taken along the line Z"-Z''' of (a) of FIG. 6. The particle separation device of Embodiment 3 includes a chip 31, which is a main part of the particle separation device, as shown in (a) of FIG. 6. The chip 31 includes at least a first inlet port 32, a first inlet flow path 41, a second inlet port 39, a second inlet flow path 40, a particle feeding section 43, a joining section 42, a separation flow path 33, a divergence section 34, a first flow path 35, a first outlet port 36, a second flow path 37, and a second outlet port 38.

Note that the chip 31 corresponds to the chip 11 of Embodiment 2, the first inlet port 32 corresponds to the first inlet port 12, the second inlet port 39 corresponds to the second inlet port 19, the joining section 42 corresponds to the joining section 22, the separation flow path 33 corresponds to the separation flow path 13, the divergence section 34 corresponds to the divergence section 14, the first flow path 35 corresponds to the first flow path 15, the first outlet port 36 corresponds to the first outlet port 16, the second flow path 37 corresponds to the second flow path 17, and the second outlet port 38 corresponds to the second outlet port 18. Therefore, structures or forms which are not particularly described in the following description are similar to those of Embodiment 2.

The first inlet flow path 41 and the second inlet flow path 40 are connected to each other via the joining section 42 so as to be smoothly curved (so as to have a curve having a certain curvature) toward the separation flow path 33. Therefore, a separation fluid or a separation fluid containing a particle group can be smoothly flown. This makes it possible to more reduce a possibility that the first inlet flow path 41 and the second inlet flow path 40 may be clogged with a particle group. Further, it is possible to efficiently disperse a particle group into a separation fluid. This makes it possible to more improve a separation accuracy of the particle separation device.

The particle feeding section 43 is an feeding port which allows a suspension containing a particle group or only a particle group to enter thereinto in order to disperse the suspension or the particle group into a separation fluid by mixing it with the separation fluid in the joining section 22 so as to supply the mixture to the separation flow path 33. A method of feeding a particle group is not particularly limited provided that the method allows the particle group to be fed. The method is, for example, (A) a method in which a suspension containing a particle group is fed from a liquid-feeding device through a tube with use of a liquid-feeding device such as a syringe pump, and (B) a method in which a particle group is directly fed from a high position by using a difference in gravity in order to prevent the separation fluid from flowing backward through the particle feeding section 43. Examples of the particle group which can be directly fed from the particle feeding section 43 encompass a gel particle group and a particle group having elasticity. By feeding a particle group through the particle feeding section 43, the particle group can be efficiently dispersed into a separation fluid. This makes it possible to more efficiently separate the particle group.

The first flow path 35 and the second flow path 37, as well as the first inlet flow path 41 and the second inlet flow path 40, are connected to each other via the divergence section 34 so as to be smoothly curved (so as to have a curve having a certain curvature) toward the separation flow path 33. Therefore, a separation fluid or a separation fluid containing a particle group can be smoothly flown. This makes it possible to more reduce a possibility that the first flow path 35 and the second flow path 37 are clogged with a particle group.

Embodiment 4

Figure 9:
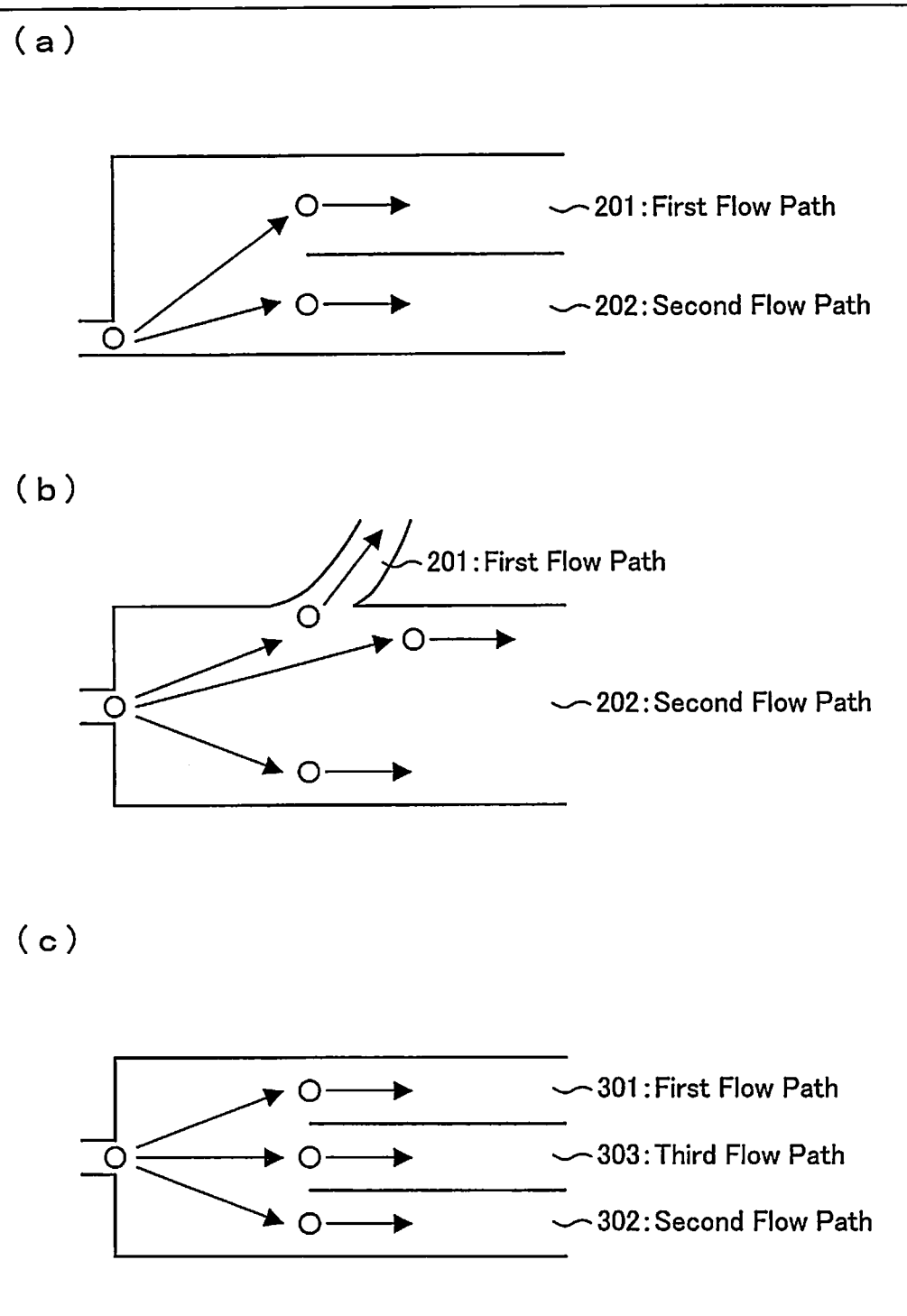

Each of the structures of the particle separation devices, which have been described in above Embodiments 1 through 3, may be any one of structures shown in FIG. 9. FIG. 9 is explanatory views each explaining a schematic structure of a modification example of a separation flow path and a divergence section. Specifically, (a) of FIG. 9 is an explanatory view illustrating a structure to separate a particle group having a density lower than that of a separation fluid. (b) of FIG. 9 is an explanatory view illustrating a structure to separate in advance a particle group having a density extremely lower than that of a separation fluid. (c) of FIG. 9 is an explanatory view illustrating a structure to separate a particle group having a density lower than that of a separation fluid, a particle group having a density higher than that of the separation fluid, and a particle group having a density closer to that of the separation fluid. Hereinafter, more specific description will be made.

In the structure of (a) of FIG. 9, a flow path diameter of an inlet port (or a divergence section) is smaller than that of a separation flow path. Therefore, two kinds of particle groups which are different in density are supplied in a falling direction (direction of gravity) from one region to a first flow path 201 and a second flow path 202. The particle group, in which the particles are different in density and have a density lower than that of the separation fluid, rise at their rising velocities in accordance with the formula (1). Under a certain condition, in accordance with the formula (1), the particle group, in which particles are different in density, are located at different heights (heights in the direction of gravity) of the divergence section located at an end of the separation flow path. That is, the particle group are separated into two particle groups: a particle group which gathers in the rising direction (direction against gravity) in the divergence section; and a particle group which gathers in the falling direction (direction of gravity) in the divergence section. Thus, the particles different in density can be separated by the first flow path 201 and the second flow path 202.

In the structure shown in (b) of FIG. 9, a flow path diameter of an inlet port (or divergence section) is smaller than that of a separation flow path, and at least two kinds of particle groups which are different in density are supplied to the second flow path 202 from one region at the center thereof. Among the particles which are different in density, a particle group having extremely lower density than that of a separation fluid rises in the rising direction (direction against gravity) at a relatively fast rising velocity. A location at a certain distance from the inlet port (or divergence section) is determined as a divergence point, and the first flow path 201 is provided in the rising direction (direction against gravity). Therefore, under a certain condition, only the particle group having an extremely lower density is supplied to the first flow path 201. Thus the particle groups can be separated. Further, it is possible to separate the rest of the particle groups by supplying such a particle group(s) to the second flow path 202. If necessary, it is possible to further separate the particle group(s) thus supplied by providing a divergence section in the second flow path 202.

In the structure shown in (c) of FIG. 9, a flow path diameter of an inlet port (or divergence section) is smaller than that of a separation flow path, and a particle group, which is a mixture of (i) a particle group having a density lower than that of a separation fluid, (ii) a particle group having a density higher than that of the separation fluid, and (iii) a particle group having a density which is closer to that of the separation fluid, is supplied to a first flow path 301, a second flow path 302, and a third flow path 303 from a certain region at the center thereof. Among the particles in the mixture, the particle group having the density lower than that of the separation fluid rises in the rising direction (direction against gravity). The particle group having the density higher than that of the separation fluid sediments in the falling direction (direction of gravity). The particle group having the density near the density of the separation fluid does not rise or sediment, and is flown through a flow path while maintaining a certain height in accordance with the formula (1). Therefore, the particle group having the density lower than that of the separation fluid is supplied to the first flow path 301 provided in the rising direction (direction against gravity), the particle group having the density higher than that of the separation fluid is supplied to the second flow path 302 in the falling direction (direction of gravity), and the particle group having the density near the density of the separation fluid is supplied to the third flow path 303 provided between the first flow path 301 and the second flow path 302 (at substantially the center). This makes it possible to separate those particle groups into the first flow path 301, the second flow path 302, and the third flow path 303.

Embodiment 5

Figure 10:
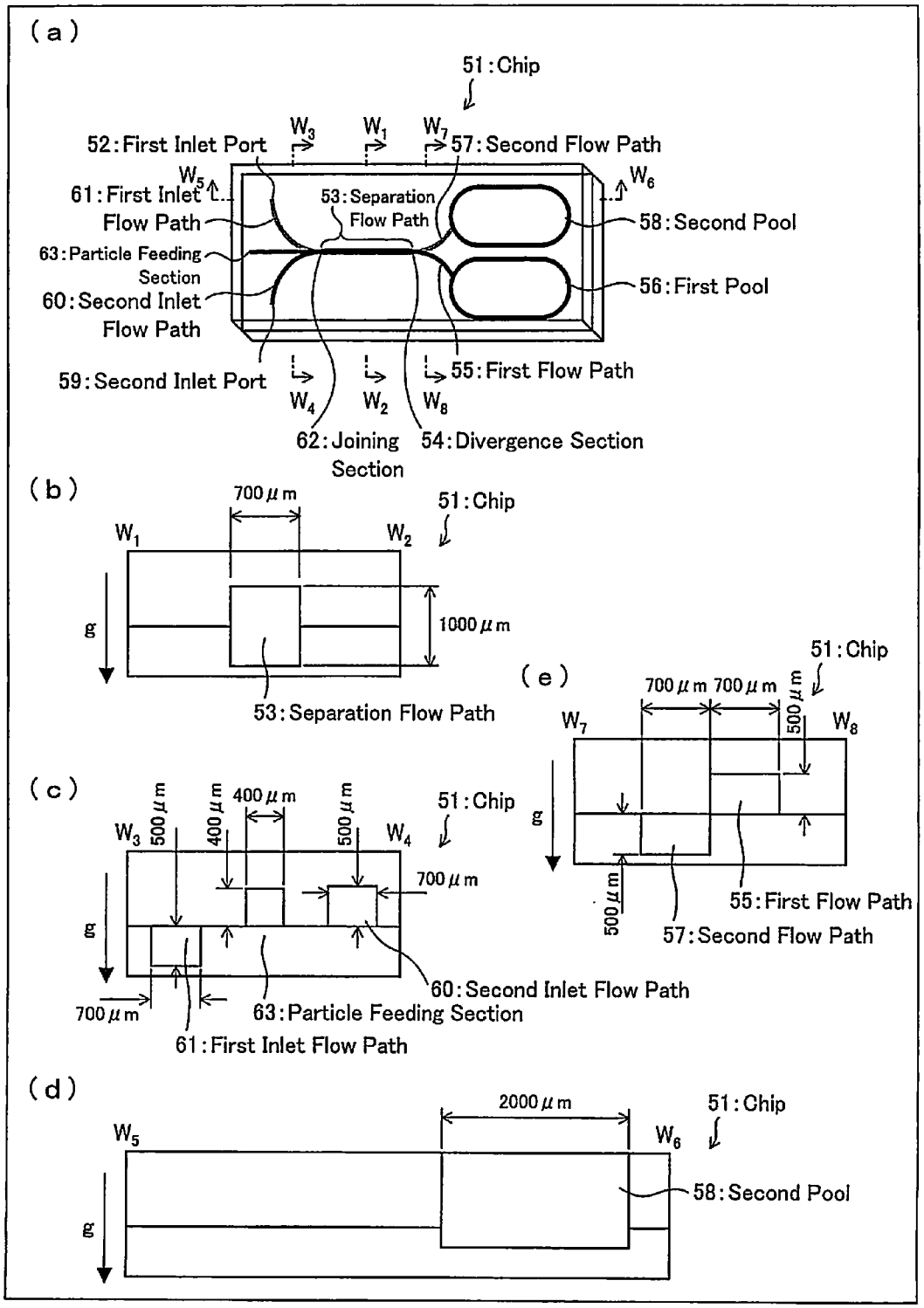

Further still another embodiment of the present invention will be described below with reference to drawings. (a) of FIG. 10 is a plan view illustrating a schematic structure of a particle separation device in Example 6 (described below). (b) of FIG. 10 is a cross-sectional view taken along the line $W_1$-$W_2$ of (a) of FIG. 10. (c) of FIG. 10 is a cross-sectional view taken along the line $W_3$-$W_4$ of (a) of FIG. 10. (d) of FIG. 10 is a cross-sectional view taken along the line $W_5$-$W_6$ of (a) of FIG. 10. (e) of FIG. 10 is a cross-sectional view taken along the line $W_7$-$W_8$ of (a) of FIG. 10. The particle separation device of Embodiment 5 includes a chip 51 which is a main part of the particle separation device as shown in (a) of FIG. 10. The chip 51 includes at least a first inlet port 52, a first inlet flow path 61, a second inlet port 59, a second inlet flow path 60, a particle feeding section 63, a joining section 62, a separation flow path 53, a divergence section 54, a first flow path 55, a first pool 56, second flow path 57, and a second pool 58.

Note that the chip 51 corresponds to the chip 31 of Embodiment 3, the first inlet port 52 corresponds to the first inlet port 32, the second inlet port 59 corresponds to the second inlet port 39, the first inlet flow path 61 corresponds to the first inlet flow path 41, the second inlet flow path 60 corresponds to the second inlet flow path 40, the joining section 62 corresponds to the joining section 42, the separation flow path 53 corresponds to the separation flow path 33, the divergence section 54 corresponds to the divergence section 34, the first flow path 55 corresponds to the first flow path 35, the first pool 56 corresponds to the first outlet port 36, the second flow path 57 corresponds to the second flow path 37, and the second pool 58 corresponds to the second outlet port 38. Therefore, structures or forms which are not particularly described in the following description are similar to those of Embodiment 3.

The first pool 56 is provided as an alternative to an outlet port for discharging a separation fluid containing a particle group having a low density which has been separated in the chip 51. The first pool 56 has a shape forming a pool for collecting a separation fluid containing a particle group which has been separated in the chip 51. Meanwhile, the second pool 58 is provided as an alternative to an outlet port for discharging a separation fluid containing a particle group having a high density which has been separated in the chip 51. The second pool 58 has a shape forming a pool for collecting the separation fluid containing the particle group which has been separated in the chip 51.

With the above structure, the particle separation device of Embodiment 5, as well as the particle separation device of Embodiment 3, can prevent contamination of separated particles, thereby separating particles more accurately.

As described above, a particle separation device of the present invention includes at least: a separation flow path (i) to which a separation fluid and a particle group including two types of particles being different in density are supplied, and (ii) through which the separation fluid flows in a certain direction; a divergence section connected to at least an end of the separation flow path in the certain direction in which the separation fluid flows, a first flow path formed from the divergence section in a rising direction; and a second flow path formed from the divergence section in a falling direction, the separation flow path being formed in a horizontal direction.

With the above structure, in accordance with the Stokes' formula, a particle group having a higher density is flown in a region in a relatively falling direction of the separation flow path through which a separation fluid is flown in a certain direction, meanwhile, a particle group having a lower density is flown in a region in a relatively rising direction of the separation flow path. Therefore, particles of the particle groups are supplied to the first flow path formed in the rising direction or the second flow path formed in the falling direction. As a result, the particles can be separated on the basis of a difference in density even if the particles have an identical diameter (size).

This makes it possible to separate a particle group for a short time without a great stress to particles and easily collect the particle group thus separated. Further, with the above structure, the particle group can be efficiently separated in accordance with flow in the separation flow path.

In the particle separation device of the present invention, it is preferable that the separation fluid have a density which is lower than a maximum density of particles of one of the two types, which particles have a low density and are to be supplied to the first flow path, and is higher than a minimum density of particles of another one of the two types, which particles have a high density and are to be supplied to the second flow path. With the above structure, the particles having the low density to be supplied to the first flow path rise whereas all particles having the high density to be supplied to the second flow path sediment in accordance with the Stokes' formula. Therefore, it is possible to provide a particle separation device which can separate particles more efficiently and more accurately.

In the particle separation device of the present invention, it is preferable that a first member, in which grooves for constituting the separation flow path, the divergence section, the first flow path, and the second flow path are made, and a second member, in which grooves for constituting the separation flow path, the divergence section, the first flow path, and the second flow path are made, be stacked on each other so that the grooves of the first member and the corresponding grooves of the second member constitute the separation flow path, the divergence section, the first flow path, and the second flow path. With the above structure, it is possible to form the particle separation device more easily. It is also possible to clean the separation flow path, the divergence section, the first flow path, and the second flow path more easily.

In the particle separation device of the present invention, it is preferable that a first member, in which grooves for constituting the separation flow path, the divergence section, and the first flow path are made, and a second member, in which grooves for constituting the separation flow path, the divergence section, and the second flow path are made, be stacked on each other so that the grooves of the first member and the corresponding grooves of the second member constitute the separation flow path, the divergence section, the first flow path, and the second flow path. With the above structure, it is possible to form the particle separation device more easily. It is also possible to clean the separation flow path, the divergence section, the first flow path, and the second flow path more easily. Furthermore, with the above structure, the first flow path and the second flow path can be formed unevenly (to have a double-layer structure) seen from the separation flow path. This makes it possible to more reduce a vertical width (height) of the particle separation device.

In the particle separation device of the present invention, it is preferable that a first member, in which grooves for constituting the separation flow path, the divergence section, the first flow path, and the second flow path are made, and a flat second member in which no groove is formed, be stacked on each other so that the grooves constitute the separation flow path, the divergence section, the first flow path, and the second flow path. With the above structure, it is possible to form the particle separation device more easily. It is also possible to clean the separation flow path, the divergence section, the first flow path, and the second flow path more easily.

In the particle separation device of the present invention, it is preferable that particles of one of the two types, which are separated into the first flow path, and another one of the two types, which are separated into the second flow path, have a minimum difference in density of at least 0.002 g/mL. The above structure can prevent contamination of separated particles, so that it is possible to provide a particle separation device that can separate particles more accurately.

In the particle separation device of the present invention, it is preferable that the separation flow path, the first flow path, and the second flow path each have a minimum diameter which is three times as large as a particle diameter of each of the particles of the particle group but is less than 1,000 times as large as the particle diameter of each of the particles. With the above structure, it is possible to more reduce a possibility that the separation flow path, the first flow path, and the second flow path are clogged with a particle group.

In the particle separation device of the present invention, it is preferable that the two types of particles of the particle group have particle diameters within a range of 1 µm to 1,000 µm. With the above structure, it is possible to separate a particle group more efficiently because the particles of the particle group satisfy the Stokes' formula more accurately. Further, the particles do not rise or sediment too quickly or too slowly, so that it is possible to provide a more practical particle separation device including a separation flow path of an appropriate length.

In the particle separation device of the present invention, it is preferable that the particle group be a group of somatic cells. With the above structure, it is possible to prevent inconvenience where, for example, a cell function of the somatic cells is reduced or an enough cell response cannot be obtained when the particles (somatic cells) are separated.

In the particle separation device of the present invention, it is preferable that the particle group be a mixture of low-quality cells and medium-quality to high-quality cells. A medium-quality to high-quality cell takes a material in at a speed faster than that of a low-quality cell, so that the medium-quality to high-quality cell has a higher density, and sediments in a separation fluid before the low-quality cell. Therefore, with the above structure, it is possible to separate the medium-quality to high-quality cell from the low-quality cell with ease, quickness, and less stimulation.

As described above, in order to achieve the above object, a method of separating particles in accordance with the present invention with use of the particle separation device, includes the step of separating a particle group into a particle group having a high density and a particle group having a low density.

With the above structure, it is possible to provide a method of separating a particle group with ease for a short time, as compared with conventional methods of separating a particle group.

EXAMPLES

Hereinafter, the present invention will be further described with Examples.

Example 1

(a) of FIG. 1 is the side view illustrating the schematic structure of the particle separation device, and (b) of FIG. 1 is the cross-sectional view taken along the line X-X' of (a) of FIG. 1. The particle separation device of Example 1 is a specific example of the particle separation device of Embodiment 1. The chip 1 was produced with use of a conventionally known producing method. That is, the chip 1 was produced as follows: polymethyl methacrylate (PMMA) resin was processed with use of a precision machine to form a shape having a rectangular recess serving as a micro flow path; a first member having grooves, a member of the chip 1, was produced from polydimethylsiloxane (PDMS) resin by using the PMMA resin having the above shape as a mold; a flat second member (glass substrate) with no grooves was produced; and the first and second members were stacked on each other. In this way, the chip 1 was produced.

The separation flow path 3 was processed so that its cross-section had a rectangular shape of 600 μm in the vertical direction and 200 μm in the horizontal direction. The separation flow path 3 was 4 cm long. The first flow path 5 and the second flow path 7 were processed so that their cross-sections had a rectangular shape of 300 μm in the vertical direction and 200 μm in the horizontal direction. The divergence section 4 was processed so as to have a vertical Y structure. In order to improve a strength of the chip 1 made from polydimethylsiloxane resin, a glass substrate for reinforcing the chip 1 was bonded to a surface (maximum surface) of the chip 1 with use of a conventionally known oxygen plasma treatment.

A particle separation device including the chip 1 which had been produced as described above was subjected to a separation evaluation test. How to perform the separation evaluation test will be described specifically below. The chip 1 was fixed so that the maximum surface was perpendicular to the direction of gravity at the time of the separation evaluation test. In other words, the chip 1 was perpendicularly fixed.

A cane sugar aqueous solution, which had been prepared to have a concentration of 1.2 g/mL, was used as a separation fluid for use in the separation evaluation test. A polyacrylamide gel, which was usually used in gel filtration, was used as a particle group for use in the separation evaluation test. Two particle groups, i.e., a polyacrylamide gel A having a low density and a polyacrylamide gel B having a high density, were used as the polyacrylamide gel. In a case where the polyacrylamide gel A was swelled by the cane sugar aqueous solution (concentration: 1.2 g/mL), a density of the polyacrylamide gel A was 1.0 g/mL or less and a particle diameter thereof was 45 μm to 90 μm. In a case where the polyacrylamide gel B was swelled by the cane sugar aqueous solution (concentration: 1.2 g/mL), a density of the polyacrylamide gel B was 1.3 g/mL or more and a particle diameter thereof was 45 μm to 90 μm.

A separation fluid containing a particle group was supplied from the inlet port 2 to the separation flow path 3 through a fluid-feeding tube with use of a syringe pump. A flow rate of the separation fluid containing particles was 4.0 μL/min, and a flow rate in the micro flow path was 3.3 cm/min. The separation fluid containing the particle group, which had been discharged from the first flow path 5 and the second flow path 7, was collected from the first outlet port 6 and the second outlet port 8, respectively, through fluid-feeding tubes. Then, a particle group was taken out from the separation fluid.

As a result of the separation evaluation test, the polyacrylamide gel A rose while flowing through the separation flow path 3, and was supplied to the first flow path 5 which was connected to the separation flow path 3 at the divergence section 4 in the rising direction. The polyacrylamide gel A was not mixed with the polyacrylamide gel B, so that only the polyacrylamide gel A was collected from the first outlet port 6. Meanwhile, the polyacrylamide gel B sedimented while flowing through the separation flow path 3, and was supplied to the second flow path 7 which was connected in the falling direction to the separation flow path 3 at the divergence section 4. The polyacrylamide gel B was not mixed with the polyacrylamide gel A, so that only the polyacrylamide gel B was collected from the second outlet port 8.

Figure 2:
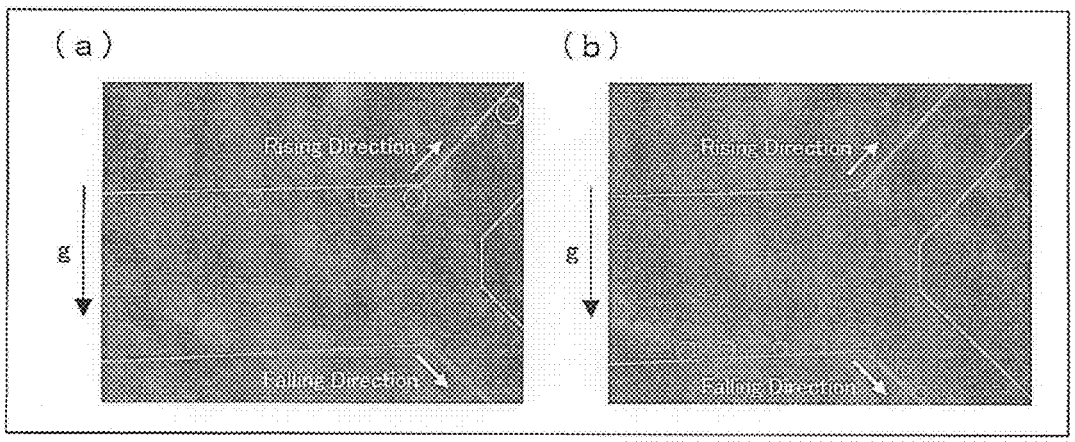

(a) of FIG. 2 and (b) of FIG. 2 are both side views each in which the divergence section 4 and a periphery of the divergence section 4 of the particle separation device to be subjected to the separation evaluation test of Example 1 are observed in a horizontal direction. In (a) of FIG. 2, the polyacrylamide gel A rose while flowing through the separation flow path 3, and was supplied to the first flow path 5 which was connected to the separation flow path 3 at the divergence section 4 in the rising direction. In (b) of FIG. 2, the polyacrylamide gel B sedimented while flowing through the separation flow path 3, and was supplied to the second flow path 7 which was connected to the separation flow path 3 at the divergence section 4 in the falling direction.

Example 2

(a) of FIG. 3 is the plan view illustrating the schematic structure of the particle separation device. (b) of FIG. 3 is the cross-sectional view taken along the line Y-Y' of (a) of FIG. 3. (c) of FIG. 3 is the cross-sectional view taken along the line Y''-Y''' of (a) of FIG. 3. A particle separation device of Example 2 is a specific example of the particle separation device of Embodiment 2. The chip 11 was produced in substantially the same way as the chip 1 of Example 1, i.e., was produced such that a first member and a second member were produced with use of molds, and the first and second members were stacked on each other.

The separation flow path 13 was processed so that its cross-section had a square shape of 400 μm in the vertical direction and 400 μm in the horizontal direction. The separation flow path 13 was 4 cm long. The first flow path 15 and the second flow path 17 were processed so that their cross-sections had a rectangular shape of 200 μm in the vertical direction and 400 μm in the horizontal direction. The joining section 22 and the divergence section 14 were processed to have a plane double-layer Y structure. That is, the joining section 22 and the divergence section 14 were formed to have a shape of Y seen in the vertical direction and to have a shape of V in three dimensions, which shape of V was formed by connecting two flow paths.

The chip 11 was fixed so that a maximum surface of the chip 11 was perpendicular to the horizontal direction during the separation evaluation test. That is, the chip 11 was horizontally fixed. A flow rate of a separation fluid containing particles was 4.0 μL/min, and a flow rate in the micro flow path was 2.5 cm/min. The separation fluid containing a particle group was introduced from both the first inlet port 12 and the second inlet port 19 at the same rate. Other conditions were identical with those of Example 1.

As a result of the separation evaluation test, the polyacrylamide gel A rose while flowing through the separation flow path 13, and was supplied to the first flow path 15 which was connected to the separation flow path 13 at the divergence section 14 in the rising direction. The polyacrylamide gel A was not mixed with the polyacrylamide gel B, so that only the polyacrylamide gel A was collected from the first outlet port 16. Meanwhile, the polyacrylamide gel B sedimented while flowing through the separation flow path 13, and was supplied to the second flow path 17 which was connected in the falling direction to the separation flow path 13 at the divergence section 14. The polyacrylamide gel B was not mixed with the polyacrylamide gel A, so that only the polyacrylamide gel B was collected from the second outlet port 18.

Figure 4:
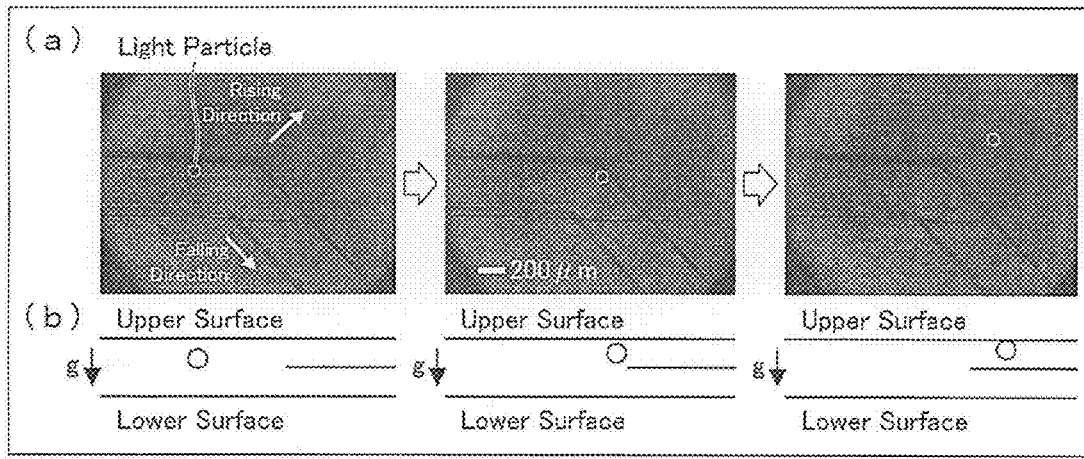
Figure 5:
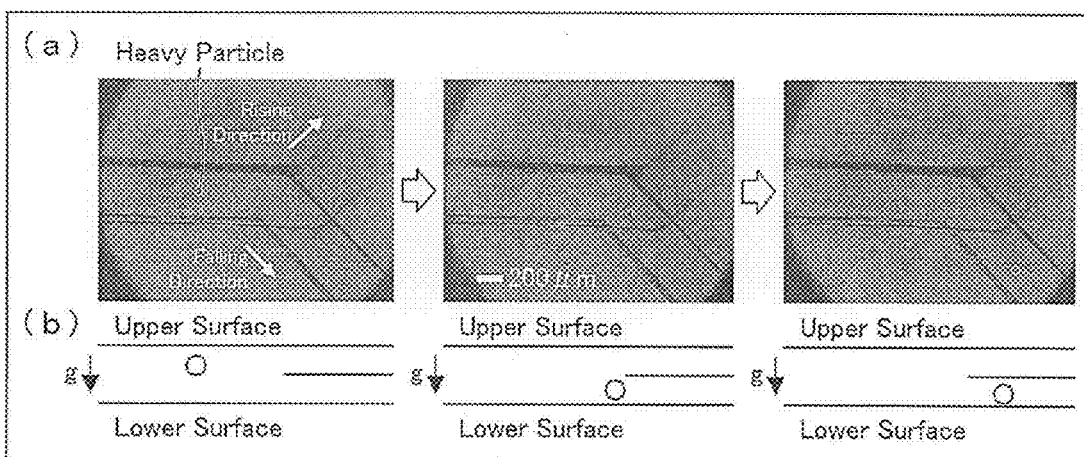

(a) of FIG. 4 and (a) of FIG. 5 are plan views each in which the divergence section 14 and a periphery of the divergence section 14 of the particle separation device to be subjected to the separation evaluation test are observed in the vertical direction. (b) of FIG. 4 and (b) of FIG. 5 are schematic cross-sectional views seen in the horizontal direction. (a) and (b) of FIG. 4 illustrate the polyacrylamide gel A which rises while flowing through the separation flow path 13 and is supplied to the first flow path 15 which is connected to the separation flow path 13 in the rising direction at the divergence section 14. (a) and (b) of FIG. 5 illustrate the polyacrylamide gel B which sediments while flowing through the separation flow path 13 and is supplied to the second flow path 17 which is connected to the separation flow path 13 in the falling direction at the divergence section 14.

Example 3

(a) of FIG. 6 is the plan view illustrating the schematic structure of the particle separation device. (b) of FIG. 6 is a cross-sectional view taken along the line Z-Z' of (a) of FIG. 6. (c) of FIG. 6 is a cross-sectional view taken along the line Z"-Z'" of (a) of FIG. 6. The particle separation device of Example 3 is a specific example of the particle separation device of Embodiment 3. The chip 31 was produced in substantially the same way as the chip 11 of Example 2.

The separation flow path 33 was processed so that its cross-section had a rectangular shape of 400 µm in the vertical direction and 700 µm in the horizontal direction. The separation flow path 33 was 4 cm long. The first inlet flow path 41, the second inlet flow path 40, the first flow path 35, and the second flow path 37 were processed so that their cross-sections had a rectangular shape of 200 µm in the vertical direction and 400 µm in the horizontal direction. The particle feeding section 43 was processed so that its cross-section had a square shape of 200 µm or 300 µm in the vertical direction and 200 µm or 300 µm in the horizontal direction. The joining section 42 and the divergence section 34 were processed to have a plane double-layer Y structure. That is, the joining section 42 and the divergence section 34 were formed to have a shape of Y seen in the vertical direction and to have a shape of V in three dimensions, which shape of V was formed by connecting two flow paths. The first inlet flow path 41 and the second inlet flow path 40 were formed to be smoothly curved (to have a curve having a certain curvature) toward the separation flow path 33 via the joining section 42. The first flow path 35 and the second flow path 37 were formed to be smoothly curved (to have a curve having a certain curvature) toward the separation flow path 33 via the divergence section 34.

A particle separation device including the chip 31 which had been produced as described above was subjected to the separation evaluation test twice. The chip 31 was fixed so that a maximum surface of the chip 31 was perpendicular to the horizontal direction during the separation evaluation test. In other words, the chip 31 was horizontally fixed.

A cane sugar aqueous solution, which had been prepared to have a concentration of 1.05 g/mL, was used as a separation fluid for use in the separation evaluation test. A polystyrene particle, which was used as a control sample with a controlled particle diameter, was used as a particle group for use in the separation evaluation test. Two kinds of particle groups, i.e., a polystyrene particle A having a low density and a polystyrene particle B having a high density, were used as the polystyrene particle. In a case where the polystyrene particle A was swelled by the cane sugar aqueous solution (concentration: 1.05 g/mL), the polystyrene particle A had a density of 1.04 g/mL to 1.05 g/mL or less and a particle diameter of 150 µm. In a case where the polystyrene particle B was swelled by the cane sugar aqueous solution (concentration: 1.05 g/mL), the polystyrene particle B had a density of 1.05 g/mL to 1.06 g/mL or more and a particle diameter of 140 µm.

A separation fluid was supplied from the first inlet port 32 and the second inlet port 39 to the separation flow path 33 through fluid-feeding tubes at the same rate with use of a syringe pump. The particle group was fed from the particle feeding section 43. A flow of the separation fluid containing the particle group was 20 µL/min, and a flow rate of the separation fluid was 7.1 cm/min in the separation flow path serving as a micro flow path. The separation fluid containing the particle group, which had been discharged from the first flow path 35 and the second flow path 37, was collected from the first outlet port 36 and the second outlet port 38, respectively, through fluid-feeding tubes. Then, the particle group was taken out from the separation fluid. Other conditions are identical to those of Example 2.

As a result of the separation evaluation test in twice, the polystyrene particle A rose while flowing through the separation flow path 33, and was supplied to the first flow path 35 which was connected in the rising direction to the separation flow path 33 at the divergence section 34. The polystyrene particle A was not mixed with the polystyrene particle B, so that only the polystyrene particle A was collected from the first outlet port 36. Meanwhile, the polystyrene particle B sedimented while flowing through the separation flow path 33, and was supplied to the second flow path 37 which was connected in the falling direction to the separation flow path 33 at the divergence section 34. The polystyrene particle B was not mixed with the polystyrene particle A, so that only the polystyrene particle B was collected from the second outlet port 38.

Figure 7:
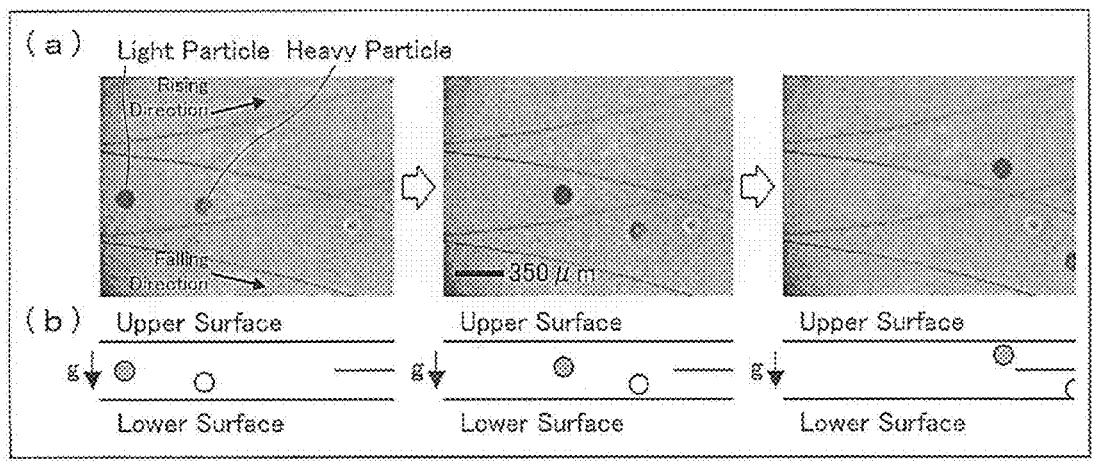

(a) of FIG. 7 is a plan view in which the divergence section 34 and a periphery of the divergence section 34 of the particle separation device for use in a separation evaluation test of Example 3 are observed in the vertical direction. (b) of FIG. 7 corresponds to (a) of FIG. 7 and is a schematic cross-sectional view seen in the horizontal direction. In (a) of FIG. 7, the polystyrene particle A rose while flowing through the separation flow path 33, and was supplied to the first flow path 35 which was connected in the rising direction to the separation flow path 33 at the divergence section 34. In (b) of FIG. 7, the polystyrene particle B sedimented while flowing through the separation flow path 33, and was supplied to the second flow path 37 which was connected in the falling direction to the separation flow path 3 at the divergence section 34.

Example 4

A chip 31 was produced in the similar way as the chip 31 of Example 3 except that the particle feeding section 43 of this example was processed so that its cross-section had a square shape of 300 µm in the vertical direction and 300 µm in the horizontal direction. A particle separation device including the chip 31 was subjected to a separation evaluation test in the similar way as the particle separation device of Example 3.

As a result of the separation evaluation test, the polystyrene particle A rose while flowing through the separation flow path 33, and was supplied to the first flow path 35 which was connected in the rising direction to the separation flow path 33 at the divergence section 34. The polystyrene particle A was not mixed with the polystyrene particle B, so that only the polystyrene particle A was collected from the first outlet port 36. Meanwhile, the polystyrene particle B sedimented while flowing through the separation flow path 33, and was supplied to the second flow path 37 which was connected in the falling direction to the separation flow path 33 at the divergence section 34. The polystyrene particle B was not mixed with the polystyrene particle A, so that only the polystyrene particle B was collected from the second outlet port 38.

Example 5

The chip 31 was produced in the similar way as the chip 31 of Example 3 except that the particle feeding section 43 of this example was processed so that its cross-section had a square shape of 200 µm in the vertical direction and 200 µm in the horizontal direction. A particle separation device including the chip 31 was subjected to a separation evaluation test in the similar way as the chip 31 of Example 3.

As a result of the separation evaluation test, the polystyrene particle A rose while flowing through the separation flow path 33, and was supplied to the first flow path 35 which was connected in the rising direction to the separation flow path 33 at the divergence section 34. The polystyrene particle A was not mixed with the polystyrene particle B, so that only the polystyrene particle A was collected from the first outlet port 36. Meanwhile, the polystyrene particle B sedimented while flowing through the separation flow path 33, and was supplied to the second flow path 37 which was connected in the falling direction to the separation flow path 33 at the divergence section 34. The polystyrene particle B was not mixed with the polystyrene particle A, so that only the polystyrene particle B was collected from the second outlet port 38.

Example 6

(a) of FIG. 10 is a plan view illustrating a schematic structure of a particle separation device. (b) of FIG. 10 is a cross-sectional view taken along the line $W_1$-$W_2$ of (a) of FIG. 10. (c) of FIG. 10 is a cross-sectional view taken along the line $W_3$-$W_4$ of (a) of FIG. 10. (d) of FIG. 10 is a cross-sectional view taken along the line $W_5$-$W_6$ of (a) of FIG. 10. (e) of FIG. 10 is a cross-sectional view taken along the line $W_7$-$W_8$ of (a) of FIG. 10. The particle separation device of Example 6 is a specific example of the particle separation device of Embodiment 5, and is a cell separation device. The chip 51 was produced in the similar way as the chip 31 of Example 3. Note, however, that grooves for constituting the particle feeding section 63 were formed only in the first member.

The separation flow path 53 was processed so that its cross-section had a rectangular shape of 1,000 μm in the vertical direction and 700 μm in the horizontal direction. The separation flow path 53 was 1 cm long. The first inlet flow path 61, the second inlet flow path 60, the first flow path 55, and the second flow path 57 were processed so that their cross-sections had a rectangular shape of 500 μm in the vertical direction and 700 μm in the horizontal direction. The particle feeding section 63 was processed so that its cross-section had a square shape of 400 μm in the vertical direction and 400 μm in the horizontal direction. The joining section 62 and the divergence section 54 were processed to have a plane double-layer Y structure. That is, the joining section 62 and the divergence section 54 were formed to have a shape of Y seen in the vertical direction and to have a shape of V in three dimensions, which shape of V was formed by connecting two flow paths. The first inlet flow path 61 and the second inlet flow path 60 were formed to be smoothly curved (to have a curve having a certain curvature) toward the separation flow path 53 via the joining section 62. The first flow path 55 and the second flow path 57 were formed to be smoothly curved (to have a curve having a certain curvature) toward the separation flow path 53 via the divergence section 54.

The first pool 56 and the second pool 58 were formed to have a size enough to collect a separated separation fluid containing a particle group.

A cell separation device including the chip 51 produced as described above was subjected to a separation evaluation test. The chip 51 was fixed so that a maximum surface of the chip 51 was perpendicular to the horizontal direction during the separation evaluation test. In other words, the chip 51 was horizontally fixed.

A cane sugar aqueous solution (containing polyvinyl alcohol of 0.05% by weight), which was prepared to have a concentration (fluid density) of 1.05 g/mL, was used as a separation fluid for use in the separation evaluation test. Ova (particle group) of cattle, having a diameter of about 150 μm, were used as a particle group for use in the separation evaluation test. The ova of the cattle were a mixture of (i) low-quality ova A (cells) having a relatively low density and (ii) medium-quality to high-quality ova B (cells) having a relatively higher density. Note that the low-quality ova A are mainly immature ova, and the medium-quality to high-quality ova B are mainly mature ova.

The separation fluid was supplied to the separation flow path 53 from the first inlet port 52 and the second inlet port 59 at the same rate through the fluid-feeding tube with use of a syringe pump. The ova (particle group) were fed from the particle feeding section 63. A flow of the separation fluid containing ova was 15 μL/min, and a flow rate of the separation fluid was 4.3 cm/min in the separation flow path serving as a micro flow path. The separation fluid containing ova, which had been discharged from the first flow path 55 and the second flow path 57, was stored in the first pool 56 and the second pool 58, respectively. After that, the ova were taken out from the separation fluid. Other conditions were identical to those of Example 3.

Figure 12:
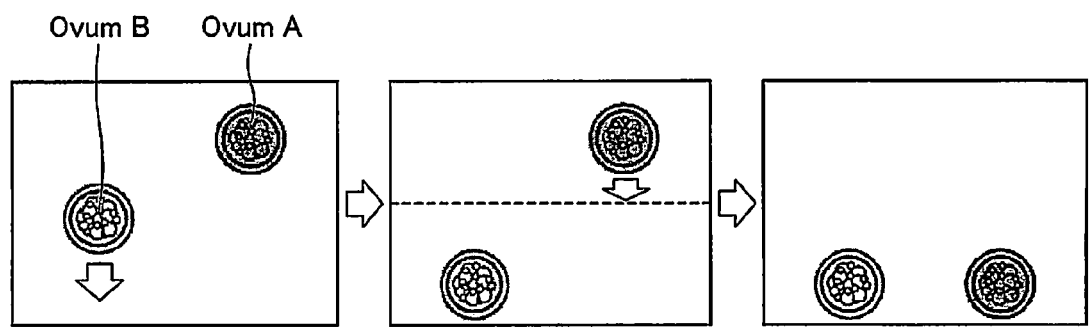
FIG. 12 is an explanatory view to explain that a low-quality ovum A and a medium-quality to high-quality ovum B in Example 6 are different in sedimentation velocity.

As a result of the separation evaluation test, the low-quality ovum A rose or slightly (slowly) sedimented while flowing through the separation flow path 53, and was supplied to the first flow path 55 which was connected in the rising direction to the separation flow path 53 at the divergence section 54. The low-quality ova A were not mixed with the medium-quality to high-quality ova B. Therefore, only the low-quality ova A were collected from the first pool 56. Meanwhile, the medium-quality to high-quality ova B rose or largely (quickly) sedimented while flowing through the separation flow path 53, and was supplied to the second flow path 57 which was connected in the falling direction to the separation flow path 53 at the divergence section 54. The medium-quality to high-quality ova B were not mixed with the low-quality ova A, and only the medium-quality to high-quality ova B were collected from the second pool 58. Therefore, as illustrated in FIG. 12, the low-quality ova A and the medium-quality to high-quality ova B were able to be separated and collected with use of a difference in sedimentation velocity (time difference).

Figure 11:
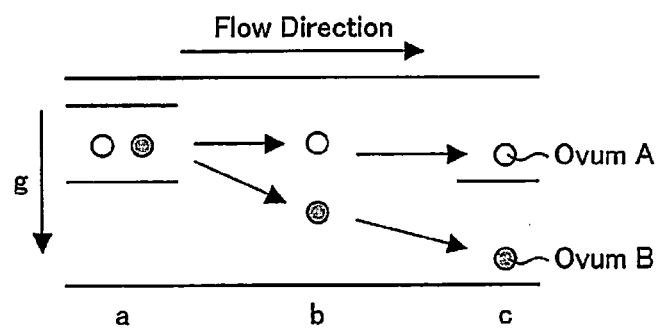
FIG. 11 is a schematic cross-sectional view in which a joining section, a separation flow path, a divergence section, and a periphery of them in the cell separation device serving as the particle separation device in Example 6 are seen in a horizontal direction.

FIG. 11 is a schematic cross-sectional view in which the joining section 62 (corresponding to a part illustrated in (c) of FIG. 10, and corresponding to 'a' shown in FIG. 11), the separation flow path 53 (corresponding to a part illustrated in (b) of FIG. 10, and corresponding to 'b' shown in FIG. 11), the divergence section 54 (corresponding to a part illustrated in (e) of FIG. 10, and corresponding to 'c' shown in FIG. 11), and a periphery of them in the cell separation device serving as a particle separation device to be subjected to a separation evaluation test are seen in the horizontal direction. The joining section 62, the separation flow path 53, and the divergence section 54 were observed with use of an inverted microscope, and it was clear from FIG. 11 that the low-quality ova A slightly rose or sedimented while flowing through the separation flow path 53, and was supplied to the first flow path 55 which was connected in the rising direction to the separation flow path 53 at the divergence section 54. Further, it was also found that the medium-quality to high-quality ova B largely sedimented while flowing through the separation flow path 53, and was supplied to the second flow path 57 which was connected in the falling direction to the separation flow path 53 at the divergence section 54.

Further, another separation evaluation test was performed while a flow rate of a separation fluid or other conditions was/were changed. (a) of FIG. 13 is a plan view in which the low-quality ovum A and the medium-quality to high-quality ovum B were observed in the vertical direction, and (b) of FIG. 13 is a plan view in which the divergence section 54 and the periphery of the divergence section 54 of the particle separation device were observed in the vertical direction.

The separation evaluation test was performed on conditions that (i) a separation fluid was fed from the first inlet port 52 and the second inlet port 59 at a flow of 40 µL/min and the separation fluid containing the ova A and B was fed from the particle feeding section 63 at a flow of 10 µL/min, (ii) a distance (travel distance of the ova A and B) between the particle feeding section 63 and the first flow path 55 or the second flow path 57 was 114 µm, (iii) a residence time of the ova A and B (a time period during which the ova A and B move 114 µm) was 8 seconds, and (iv) fifty ova were supplied from the particle feeding section 63.

As a result, twenty-three ova were collected from the first pool 56, and twenty-seven ova were collected from the second pool 58. (b) of FIG. 13 illustrates a state in which the ova slightly or largely sedimented while flowing through the separation flow path 53 and were supplied to the first flow path 55 or the second flow path 57 which was connected in the vertical direction to the separation flow path 53 at the divergence section 54.

The ova thus collected were used for in-vitro fertilization, and development of the fertilized eggs were checked. As a result, the ovum/ova collected by the first pool 56 was/were the low-quality ovum/ova A, and the ovum/ova collected by the second pool 58 was/were the medium-quality to high-quality ova B.

Meanwhile, another separation evaluation test was performed on conditions that (i) a separation fluid was fed from the first inlet port 52 and the second inlet port 59 at a flow of 20 µL/min and a separation fluid containing the ova A and B was fed from the particle feeding section 63 at a flow of 10 µL/min, (ii) a travel distance was 191 µm, (iii) a residence time was 14 seconds, and (iv) twenty-three ova were supplied. As a result, all the ova sedimented and were collected by the second pool 58.

Therefore, it is possible to separate the low-quality ova A and the medium-quality to high-quality ova B and collect them by controlling a residence time with use of a cell separation device.

INDUSTRIAL APPLICABILITY

A particle separation device and a method of separating particles in accordance with the present invention, particles of a particle group differently move in the direction of gravity on the basis of a difference in density. Therefore, even if the particles have an identical particle diameter (size), it is possible to separate and collect the particles which are different in density. This makes it possible to easily separate the particle group for a short time without a great stress (such as a gravity load) to particles, and to easily collect a selected particle group. The particle separation device and the method of separating particles in accordance with the present invention can be particularly suitable for separating a particle group such as bioparticles (e.g., somatic cells, erythrocytes, platelets, bacteria, yeast fungi, cell fractions, lipid particles, protein micelles, planktons, and algae), resin particles, and metal particles.

REFERENCE SIGNS LIST 3 separation flow path
4 divergence section
5 first flow path
7 second flow path
13 separation flow path
14 divergence section
15 first flow path
17 second flow path
33 separation flow path
34 divergence section
35 first flow path
37 second flow path
56 first pool
58 second pool

The invention claimed is:

1. A particle separation device comprising at least:
a separation flow path (i) to which a separation fluid containing a particle group including two types of particles being different in density is supplied, and (ii) through which the separation fluid flows in a certain direction;
a divergence section connected to at least an end of the separation flow path in the certain direction in which the separation fluid flows,
a first flow path formed from the divergence section in a rising direction;
a second flow path formed from the divergence section in a falling direction;
a first pool for collecting the separation fluid containing the particle group which flows through the first flow path; and
a second pool for collecting the separation fluid containing the particle group which flows through the second flow path,
wherein the separation flow path is formed in a horizontal direction, and
wherein the divergence section has a plane double-layer Y structure wherein the first flow path and the second flow path are: (i) provided in two layers, respectively; (ii) branched to form a Y shape; and (iii) parallel to a maximum surface of a chip included in the particle separation device.

2. The particle separation device as set forth in claim 1, wherein the separation fluid has a density which is lower than a maximum density of particles of one of the two types, which particles have a low density and are to be supplied to the first flow path, and is higher than a minimum density of particles of another one of the two types, which particles have a high density and are to be supplied to the second flow path.

3. The particle separation device as set forth in claim 1, wherein a first member, in which grooves for constituting the separation flow path, the divergence section, the first flow path, and the second flow path are made, and a second member, in which grooves for constituting the separation flow path, the divergence section, the first flow path, and the second flow path are made, are stacked on each other so that the grooves of the first member and the corresponding grooves of the second member constitute the separation flow path, the divergence section, the first flow path, and the second flow path.

4. The particle separation device as set forth in claim 1, wherein a first member, in which grooves for constituting the separation flow path, the divergence section, and the first flow path are made, and a second member, in which grooves for constituting the separation flow path, the divergence section, and the second flow path are made, are stacked on each other so that the grooves of the first member and the corresponding grooves of the second member constitute the separation flow path, the divergence section, the first flow path, and the second flow path.

5. The particle separation device as set forth in claim 1, wherein a first member, in which grooves for constituting the separation flow path, the divergence section, the first flow path, and the second flow path are made, and a flat second member in which no groove is formed, are stacked on each other so that the grooves constitute the separation flow path, the divergence section, the first flow path, and the second flow path.

6. The particle separation device as set forth in claim 1, wherein particles of one of the two types, which are separated into the first flow path, and another one of the two types, which are separated into the second flow path, has a minimum difference in density of at least 0.002 g/mL.

7. The particle separation device as set forth in claim 1, wherein the separation flow path, the first flow path, and the second flow path each have a minimum diameter which is three times as large as a particle diameter of each of the particles of the particle group but is less than 1,000 times as large as the particle diameter of each of the particles.

8. The particle separation device as set forth in claim 1, wherein the two types of particles of the particle group have particle diameters within a range of 1 μm to 1,000 μm.

9. The particle separation device as set forth in claim 1, wherein the particle group is a group of somatic cells.

10. The particle separation device as set forth in claim 9, wherein the particle group is a mixture of low-quality cells and medium-quality to high-quality cells.

11. A method of separating particles with use of a particle separation device as recited in claim 1, the method comprising the step of separating a particle group into a particle group having a high density and a particle group having a low density.

* * * * *